United States Patent [19]
Tachibana et al.

[11] Patent Number: 6,135,976
[45] Date of Patent: Oct. 24, 2000

[54] METHOD, DEVICE AND KIT FOR PERFORMING GENE THERAPY

[75] Inventors: Cozier Tachibana, Fukuoka, Japan; Douglas R. Hansmann, Bainbridge Island, Wash.

[73] Assignee: Ekos Corporation, Bothell, Wash.

[21] Appl. No.: 09/161,063

[22] Filed: Sep. 25, 1998

[51] Int. Cl.[7] .............................. A61N 1/30; A61M 29/00
[52] U.S. Cl. ....................................... 604/21; 604/101.03
[58] Field of Search .................................. 604/20–22, 96, 604/49, 101, 96.01, 101.01, 101.03, 101.05; 600/437, 462, 466, 467, 469, 470; 606/27–28; 607/96, 97

[56] References Cited

U.S. PATENT DOCUMENTS

| | | | |
|---|---|---|---|
| 3,433,226 | 3/1969 | Boyd | 128/305 |
| 3,565,062 | 2/1971 | Kurls | 128/24 |
| 3,938,502 | 2/1976 | Bom | 128/2 |
| 4,692,139 | 9/1987 | Stiles | 604/22 |
| 4,698,058 | 10/1987 | Greenfeld et al. | 604/266 |
| 4,808,153 | 2/1989 | Parisi | 604/22 |
| 4,870,953 | 10/1989 | DonMichael et al. | 128/24 A |
| 4,936,281 | 6/1990 | Stasz | 128/660.03 |
| 4,948,587 | 8/1990 | Kost et al. | 424/435 |
| 5,053,044 | 10/1991 | Mueller et al. | 606/159 |
| 5,085,662 | 2/1992 | Willard | 606/159 |
| 5,117,831 | 6/1992 | Jang et al. | 128/662.06 |
| 5,163,421 | 11/1992 | Bernstein et al. | 128/24.1 |
| 5,181,920 | 1/1993 | Mueller et al. | 606/159 |
| 5,197,946 | 3/1993 | Tachibana | 604/22 |
| 5,267,954 | 12/1993 | Nita | 604/22 |
| 5,267,985 | 12/1993 | Shimada et al. | 604/290 |
| 5,269,297 | 12/1993 | Weng et al. | 128/24 AA |
| 5,279,546 | 1/1994 | Mische et al. | 604/22 |
| 5,282,785 | 2/1994 | Shapland et al. | 604/21 |
| 5,286,254 | 2/1994 | Shapland et al. | 604/21 |
| 5,304,115 | 4/1994 | Pflueger et al. | 604/22 |

(List continued on next page.)

FOREIGN PATENT DOCUMENTS

| | | |
|---|---|---|
| 0 189 329 A2 | 7/1986 | European Pat. Off. . |
| 3-63041 | 3/1991 | Japan . |
| WO 90/01300 | 2/1990 | WIPO . |
| WO 91/19529 | 12/1991 | WIPO . |
| WO 94/05361 | 3/1994 | WIPO . |
| WO 94/28873 | 12/1994 | WIPO . |
| WO 97/40679 | 11/1997 | WIPO . |
| WO 98/09571 | 3/1998 | WIPO . |
| WO 98/18391 | 5/1998 | WIPO . |
| WO 98/58699 | 12/1998 | WIPO . |

OTHER PUBLICATIONS

Rosenschein, U. et al., "Experimental Ultrasonic Angioplasty: Disruption of Atherosclerotic Plaques and Thrombi in Vitro and Arterial Recanalization in Vivo", *JACC*, vol. 15, No. 3, Mar. 1, 1990, pp. 711–717.

Yumita, N. et al., "Synergistic Effect of Ultrasound and Hematoporphyrin on Sarcoma 180", *Jpn,. J. Cancer Res.*, vol. 81, No. 3, Mar. 1990, pp. 304–308.

Tachibana, K., "Enhancement of Fibrinolysis with Ultrasound Energy", *JVIR*, vol. 3, No. 2, May 1992, pp. 299–303.

*Primary Examiner*—Sharon Kennedy
*Attorney, Agent, or Firm*—David J. Weitz; Wilson Sonsini Goodrich & Rosati

[57] ABSTRACT

A catheter is provided for performing gene therapy on a selected section of a body lumen. The catheter comprises a distal catheter body including one or more expandable members for occluding sections of the body lumen proximal and/or distal to the selected section of the body lumen; a gene therapy composition delivery lumen connected to one or more gene therapy composition delivery ports at the distal catheter body for delivering a gene therapy composition to the selected section of the body lumen, the gene therapy composition delivery lumen housing a gene therapy agent; a washing lumen connected to one or more washing ports for delivering fluid to wash the selected section of the body lumen; and an ultrasound transducer for delivering ultrasound energy to the selected section of the body lumen.

14 Claims, 21 Drawing Sheets

U.S. PATENT DOCUMENTS

| | | | |
|---|---|---|---|
| 5,315,998 | 5/1994 | Tachibana et al. | 128/660.01 |
| 5,318,014 | 6/1994 | Carter | 601/2 |
| 5,324,255 | 6/1994 | Passafaro et al. | 604/22 |
| 5,328,470 | 7/1994 | Nabel et al. | 604/101 |
| 5,342,292 | 8/1994 | Nita et al. | 604/22 |
| 5,344,395 | 9/1994 | Whalen et al. | 604/22 |
| 5,362,309 | 11/1994 | Carter | 604/22 |
| 5,380,273 | 1/1995 | Dubrul et al. | 604/22 |
| 5,397,301 | 3/1995 | Pflueger et al. | 604/22 |
| 5,498,238 | 3/1996 | Shapland et al. | 604/53 |
| 5,569,198 | 10/1996 | Racchini | 604/96 |
| 5,586,982 | 12/1996 | Abela | 606/28 |
| 5,588,962 | 12/1996 | Nicholas et al. | 604/52 |
| 5,648,098 | 7/1997 | Porter | 424/490 |
| 5,735,811 | 4/1998 | Brisken | 604/22 |
| 5,925,016 | 7/1999 | Chornenky et al. | 604/101 |
| 6,030,374 | 2/2000 | McDaniel | 604/506 |

METHOD, DEVICE AND KIT FOR PERFORMING GENE THERAPY

BACKGROUND OF THE INVENTION

1. Field of the Invention

The present invention relates to devices, kits and methods for performing gene therapy, and more particularly to devices, kits and methods for performing gene therapy on an isolated region of a body lumen.

2. Description of Related Art

A living organism may suffer damage to its body lumens for a variety of reasons including normal deterioration, traumatic injury, and disease induced degradation. One particular area of concern is damage due to vascular disease, which affects a large segment of the human population where the leading cause of death is due to ischemic heart disease. Examples of current treatments for vascular disease include treating the vessels to remove damaged portions surgically, and treating damaged portions with balloon angioplasty to improve the performance of damaged tissues. During the course of balloon angioplasty, physical damage to body lumens is often a critical side effect of the treatment which results in restenosis. Other procedures lead to vessel trauma as well, for example vein bypass graft stenosis, prosthetic graft stenosis, and damage from other procedures. There are also several systemic-physiological problems that can lead to degradation of the body lumens including atherosclerosis, hypertension, angiogenesis, myocardial hypertrophy, and vascular smooth muscle cell (VSMC) hypertrophy. For example, in the case of chronic hypertension, it is thought that multiple factors play a role in determining susceptibility and degree of the problem.

Research on the vascular response to injury reveals that it involves alteration of several cellular processes: cell growth, cell migration and extracellular matrix production. This vascular response to injury is characteristic of the pathogenesis of various vascular diseases. For example, atherosclerotic lesions evolve as a result of vascular smooth muscle migration into the subintimal space, proliferation and the production of abundant extracellular matrix. In a similar fashion, restenosis after angioplasty, vein bypass graft stenosis, prosthetic graft stenosis, angiogenesis and hypertension all involve abnormalities in vascular cell growth, migration and matrix composition.

Several drugs are currently being used to treat vascular disease. However, one challenge to such drug treatments has been the development of a satisfactory method for delivering the drug to an effected segment of the body lumen. In the case of blood vessels, systemic delivery via the blood coursing through the vessel lumen is, of course, the most obvious route. However, many, if not most, of the proposed drugs have systemic side-effects which do not permit high dosages. Hence, the amount of drug available in the bloodstream will be small, resulting in a small concentration gradient in to the vessel wall.

One approach has been to insert a fluid delivery catheter into the lumen of a distal or proximal branch of the affected vessel and advance the drug delivery port to the vicinity of the lesion and then delivery a drug at high location concentration. One disadvantage of this technique is that the drug will only be at the lesion site for a short period of time since blood flow will rapidly sweep the drug downstream.

Catheters have also been used which include a balloon to occlude the lumen proximal and/or distal to the lesion to temporarily stop vessel flow during the treatment period. The disadvantage of this approach is that the patient may not be able to tolerate the stoppage of blood flow for more than a few minutes. It is thus important for the drug to be delivered and absorbed in as short a period as possible.

A need currently exists for improved devices, kits and methods for delivering drugs to vessel wall to treat vessel wall disease. Provided herein are embodiments of improved devices, kits and methods.

SUMMARY DESCRIPTION OF THE INVENTION

A catheter is provided for performing gene therapy on a selected section of a body lumen. The catheter includes a distal catheter body including one or more expandable members for occluding sections of the body lumen proximal and/or distal to the selected section of the body lumen; a gene therapy composition delivery lumen connected to one or more gene therapy composition delivery ports at the distal catheter body for delivering a gene therapy composition to the selected section of the body lumen, the gene therapy composition delivery lumen containing a gene therapy agent; and an ultrasound element for delivering ultrasound energy to the selected section of the body lumen. The catheter may optionally further include a washing lumen connected to one or more washing ports for delivering fluid to wash the selected section of the body lumen.

A kit is also provided for performing gene therapy on a selected section of a body lumen. The kit includes a gene therapy composition including a gene therapy agent; and a catheter including a distal catheter body including one or more expandable members for occluding sections of the body lumen proximal and/or distal to the selected section of the body lumen, a gene therapy composition delivery lumen connected to one or more gene therapy composition delivery ports at the distal catheter body for delivering a gene therapy composition to the selected section of the body lumen, and an ultrasound element for delivering ultrasound energy to the selected section of the body lumen. The catheter in the kit may optionally further include a washing lumen connected to one or more washing ports for delivering fluid to wash the selected section of the body lumen.

A method is also provided for performing gene therapy on a selected section of a body lumen. According to the method, a catheter is placed within a selected section of a body lumen, the catheter including one or more expandable members for occluding sections of the body lumen proximal and/or distal to the selected section. When a plurality of expandable members are employed, the expandable members are preferably independently expandable. This allows sections of the body lumen proximal, distal, or proximal and distal to the selected section of the body lumen to be occluded. A gene therapy composition is then delivered into the selected section of the body lumen. Ultrasound is then delivered to the selected section of the body lumen in the presence of the gene therapy composition.

BRIEF DESCRIPTION OF THE DRAWINGS

FIG. 1O illustrates another embodiment of the method which utilizes a catheter such as the ones illustrated in FIGS. 1D–1M which includes an expandable member which is positioned at the selected section of the body lumen.

DETAILED DESCRIPTION OF THE INVENTION

Figure 1A:
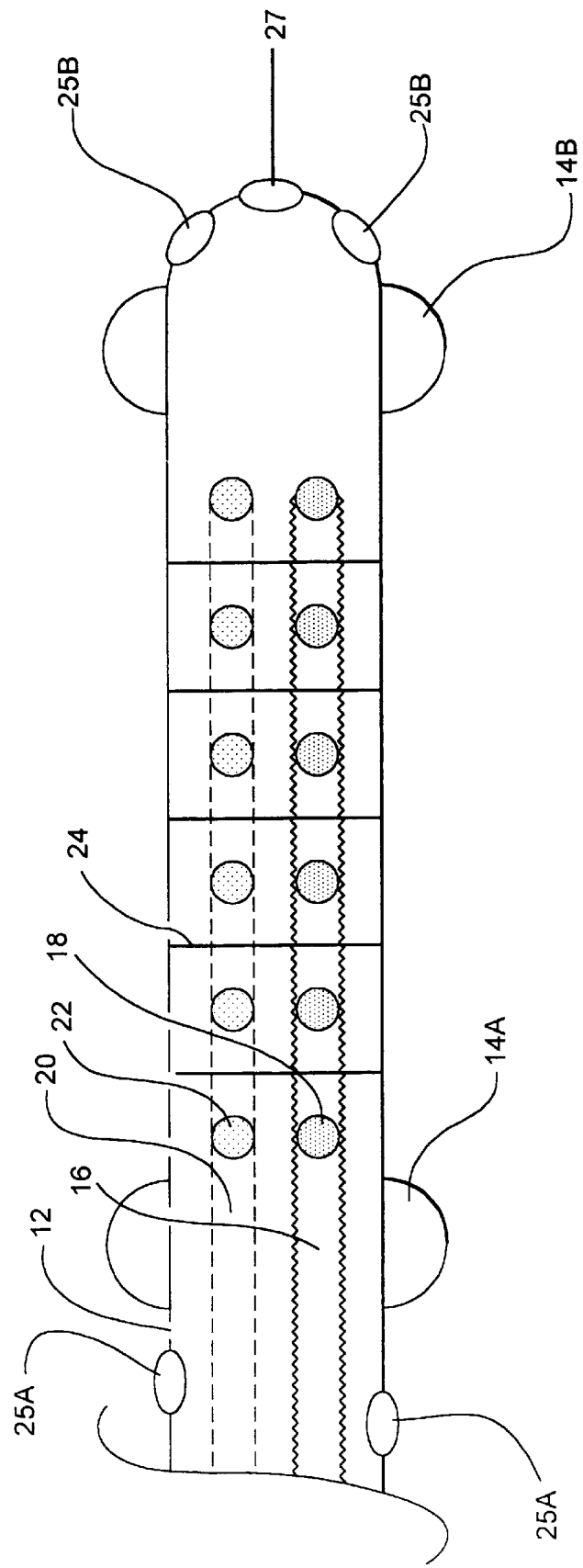
FIG. 1A illustrates a catheter with proximal and distal expandable members which may be used in the present invention.

The present invention relates to the use of ultrasound to assist the entry of a gene therapy agent into a cell in a selected section of a body lumen in order to transform the cell and express a gene product encoded by the gene therapy agent in the cell. In one particular embodiment, the selected section of the body lumen is in a diseased or injured state. For example, the selected section of the body lumen may be a section of the body lumen which is suffering from atherosclerosis or has undergone restenosis. In another particular embodiment, the selected section of the body lumen has been injured by the performance of a medical procedure adjacent the section. Balloon angioplasty and rotational atherectomy are two examples of medical procedures which are known to cause injuries to a section of a body lumen.

According to the present invention, the rate at which a gene therapy agent is absorbed into cells in the selected section of the body lumen is accelerated by the application of ultrasound to the selected section. In some instances, entry of the gene therapy agent is made possible by the application of ultrasound. It is believed that accelerated absorption of the gene therapy agent is due to cavitation of the cell membrane.

Also according to the invention, ultrasound is believed to facilitate the passage of a gene therapy agent between cells so that the gene therapy agent may be absorbed by cells which are not at the surface of the body lumen. Accordingly, a feature of the present invention is the use of ultrasound to assist the entry of a gene therapy agent into cells which are not at a surface of a body lumen in order to transform the cell and express a gene product encoded by the gene therapy agent in the cell.

In one embodiment of the invention, a gene therapy composition is provided for use in the present invention. In one variation, the composition includes a gene therapy agent. In another variation, the composition includes a gene therapy agent and a microbubble booster. In yet another variation, the composition includes a gene therapy agent and a gene therapy agent carrier. In yet another variation, the composition includes a gene therapy agent, a microbubble booster, and a gene therapy agent carrier.

In another embodiment of the invention, a kit for performing gene therapy is provided which includes an ultrasound catheter and a gene therapy composition containing a gene therapy agent. The kit may optionally further include a microbubble booster and/or a gene therapy agent carrier. The microbubble booster and/or the gene therapy agent carrier may be housed separately in the kit or may be mixed into the gene therapy composition.

In yet another embodiment of the invention, catheters are provided for performing gene therapy on a selected section of a body lumen.

In one embodiment, the catheter includes a distal catheter body including one or more expandable members for occluding sections of the body lumen proximal and/or distal to the selected section of the body lumen; a gene therapy composition delivery lumen connected to one or more gene therapy composition delivery ports in the distal catheter body for delivering a gene therapy composition to the selected section of the body lumen, the gene therapy composition delivery lumen containing a gene therapy agent; and an ultrasound element for delivering ultrasound energy to the selected section of the body lumen.

According to this embodiment, the catheter may include a single expandable member for occluding the body lumen either proximal or distal to the selected section of the body lumen. Alternatively, the catheter may include proximal and distal expandable members which occlude sections of the body lumen both proximal and distal to the selected section of the body lumen.

In another embodiment, the catheter includes a distal catheter body including an expandable member for occluding the selected section of the body lumen; a gene therapy composition delivery lumen connected to one or more gene therapy composition delivery ports in the distal catheter body for delivering a gene therapy composition to the selected section of the body lumen through the expandable member, the gene therapy composition delivery lumen containing a gene therapy agent; and an ultrasound element for delivering ultrasound energy to the selected section of the body lumen. According to this embodiment, types of expandable members that may be used include, but are not limited to a porous balloon, a microporous balloon, a macroporous balloon, a balloon within a balloon, a channeled balloon, an infusion sleeve, a hydrogel balloon, an iontophoretic balloon, or a coated stent on the outside of a balloon. Examples of these types of expandable members are described in *Eur Heart J.*, 16 437–440 (1995) which is incorporated herein by reference.

In yet another embodiment, the catheter includes a distal catheter body including one or more injection needles extendable from and retractable into the catheter body for injecting a gene therapy composition into the selected section of the body lumen; a gene therapy composition delivery lumen connected to the one or more injection needles for delivering a gene therapy composition to the one or more injection needles, the gene therapy composition delivery lumen containing a gene therapy agent; and an ultrasound element for delivering ultrasound energy to the selected section of the body lumen.

In any of the above catheter embodiments, the catheter may also optionally include a washing lumen connected to one or more washing ports for delivering fluid to wash the selected section of the body lumen.

In yet another embodiment of the invention, a method is provided for performing gene therapy on a selected section of a body lumen.

In one embodiment, the method includes placing within a selected section of the body lumen a catheter including one or more expandable members for occluding sections of the body lumen proximal and/or distal to the selected section; occluding sections of the body lumen proximal and/or distal to the selected section of the body lumen; delivering a gene therapy composition into the selected section of the body lumen; and delivering ultrasound to the selected section of the body lumen for a period of time in the presence of the gene therapy composition. According to this embodiment, the catheter may include a single expandable member for occluding the body lumen either proximal or distal to the selected section of the body lumen. Alternatively, the catheter may include proximal and distal expandable members which occlude sections of the body lumen both proximal and distal to the selected section of the body lumen.

In another embodiment, the method includes placing within a selected section of the body lumen a catheter including an expandable member for occluding the selected section; delivering a gene therapy composition to the selected section of the body lumen through the expandable member; and delivering ultrasound to the selected section of the body lumen for a period of time in the presence of the gene therapy composition. According to this embodiment, types of expandable members that may be used include, but are not limited to a porous balloon, a microporous balloon, a macroporous balloon, a balloon within a balloon, a channeled balloon, an infusion sleeve, a hydrogel balloon or a coated stent on the outside of a balloon. Examples of these types of expandable members are described in *Eur Heart J.*, 16 437–440 (1995) which is incorporated herein by reference.

According to any of the above method embodiments, the method may optionally further include the step of washing the selected section of the body lumen before delivering the gene therapy composition into the selected section of the body lumen. The method may also optionally further include the step of washing the selected section of the body lumen after delivering the gene therapy composition into the selected section of the body lumen in order to remove the gene therapy composition from the body lumen. Ultrasound, and optionally a microbubble booster, may be delivered to the selected section during the washing step(s) before and/or after delivery of the gene therapy composition. It is believed that the use of ultrasound during a washing step before delivery of a gene therapy agent prepares the selected section of the body lumen for entry of the gene therapy agent.

1. Gene Therapy Agents

As used herein, a gene therapy agent refers to any nucleic acid construct which is capable of transforming a cell in or adjacent to the body lumen. Transformation refers to the process of changing the genotype of a recipient cell by the stable introduction of RNA or DNA by whatever methodology available to one of ordinary skill in the art. According to the present invention, any gene therapy agent which is capable of transforming a cell may be used.

The nucleic acid construct may be an RNA or DNA construct. Examples of types of nucleic acid constructs which may be used as the gene therapy agent include, but are not limited to strands or duplexes of DNA and RNA, DNA and RNA viral vectors and plasmids.

The gene therapy agent may encode a gene product, i.e., a protein encoded by the nucleic acid construct which, when expressed in the cell, has a desired therapeutic effect on the cell. Examples of therapeutic effects which may be achieved include, but are not limited to, inducing cell growth, and inducing cell death.

The gene therapy agent may also include a promoter which is inserted into the genome of the cell in order to regulate the expression of a native protein in the cell. Regulation may involve increasing or decreasing the expression of the native protein by the cell.

Particular examples of gene therapy agents which may be used in the present invention include, but are not limited to those agents described in U.S. Pat. Nos. 5,719,131; 5,714,353; 5,656,465; 5,583,362; 5,399,346; 5,334,761; 5,283,185; 5,264,618; 5,252,479; 4,394,448; each of which are incorporated herein by reference in their entirety.

2. Carrier For Assisting Gene Therapy Agent Transfection

Transfection of a cell with a gene therapy agent can be facilitated through the use of a carrier in combination with the gene therapy agent. Various different carriers have been developed for performing this function. Examples of different carriers which may be used include, but are not limited to, cationic lipids (derivatives of glycerolipids with a positively charged ammonium or sulfonium ion-containing headgroup; e.g., U.S. Pat. No. 5,711,964); cationic amphiphiles (e.g., U.S. Pat. Nos. 5,719,131; 5,650,096); cationic lipids (e.g., U.S. Pat. Nos. 5,527,928; 5,283,185; 5,264,618); and liposomes (e.g., U.S. Pat. Nos. 5,711,964;

5,705,385; 5,631,237), each of the U.S. Patents listed above being incorporated herein by reference.

3. Microbubble Booster For Assisting Transfection

A microbubble booster may be used to facilitate entry of the gene therapy agent into cells. A wide variety of microbubble boosters have been developed for use in other ultrasound applications, any of which may be used in the present invention. The gene therapy agent may be separate from, attached to the surface of, or included within the microbubbles. The microbubble booster preferably comprises a liquid containing microbubbles of a gas having a diameter of 0.1 to 100 $\mu$m. The booster also preferably contains about $4\times10^7$ of the microbubbles per one milliliter of a liquid.

The microbubble booster may be formed by entrapping microspheres of a gas into a liquid. Microbubbles may be made using a variety of gases including, but not limited to air, oxygen, carbon dioxide, nitrogen, noble gases (e.g. xenon, krypton, argon, neon, helium, etc.), preferably air and oxygen gas. The liquid may include any liquid which can form microbubbles, for example, human serum albumin (e.g. 3 to 5% human serum albumin), a physiological saline solution, a 5% aqueous glucose solution, an aqueous indocyanine green solution, autoblood, an aqueous solution of maglumine diatriazoate (=renografin), and any other X-ray contrast medium).

The microbubble booster can be prepared by any known method. For example, the microbubble booster can be formed by agitating a suitable liquid while blowing a suitable gas into the liquid, or alternatively exposing the liquid to ultrasound with a sonicator under a gaseous atmosphere, whereby a vibration is given to the liquid to form microbubbles of the gas.

When the ultrasound is applied to in the presence of microbubbles, the microbubbles can act as a nucleus of cavitation and thereby the cavitation occurs more easily. This enables less ultrasonic energy to be used in order to achieve the desired amount of diffusion of the gene therapy agent into the cells.

4. Catheters For Delivering Gene Therapy Agent To Selected Section Of A Body Lumen A catheter is used to deliver the gene therapy agent to a selected section of a body lumen. In general, any catheter may be used which includes a mechanism for delivering a gene therapy composition to a selected section of the body lumen; and a mechanism for delivering ultrasound energy to the isolated section of the body lumen. It is preferred that the mechanism for delivering the gene therapy composition to the selected section of the body lumen be designed so that it maintains the gene therapy composition at or adjacent to the selected section in a relatively high, undiluted concentration, for example, at or near the concentration that the gene therapy composition was delivered.

The catheter can be used in various body lumens including, but not limited to, the blood vessels, pancreas, sinuses, esophagus, rectum, vessels adjacent the prostate, vessels in or adjacent to the brain, gastrointestinal vessels and urological vessels. The catheter is selected from a variety of different sizes, diameter and length, depending on the type and location of the lesion.

FIG. 1A illustrates an embodiment of a catheter which may be used in the present invention. As illustrated, the catheter includes a distal catheter body 12 with proximal and distal expandable members 14A, 14B for occluding sections of a body lumen proximal and distal to a selected section of the body lumen. The catheter also includes a gene therapy composition delivery lumen 16 which terminates in one or more gene therapy composition delivery ports 18 at the distal catheter body 12. The gene therapy composition delivery ports 18 are preferably positioned relative to the one or more expandable members 14A, 14B such that a gene therapy composition is delivered into the body lumen between the proximal and distal occluded sections of the body lumen.

The catheter also includes a wash lumen 20 which terminates in one or more washing ports 22 at the distal catheter body 12. The washing ports 22 are preferably positioned relative to the one or more expandable members 14A, 14B such that a washing fluid, such as saline or a microbubble booster, may be delivered into the body lumen between the proximal and distal occluded sections of the body lumen. The washing fluid can be used to wash the selected section of the body lumen prior to delivery of the gene therapy composition, for example to remove blood from the selected section. The washing fluid can also be used to wash the selected section of the body lumen after delivery of the gene therapy composition in order to remove non-absorbed gene therapy composition from the selected section of the body lumen. Ultrasound energy is optionally delivered during the washing step(s). Although not shown, the catheter can also include a bypass lumen to allow fluid to pass through the lumen while the lumen is occluded that would otherwise pass through the lumen.

Figure 1B:
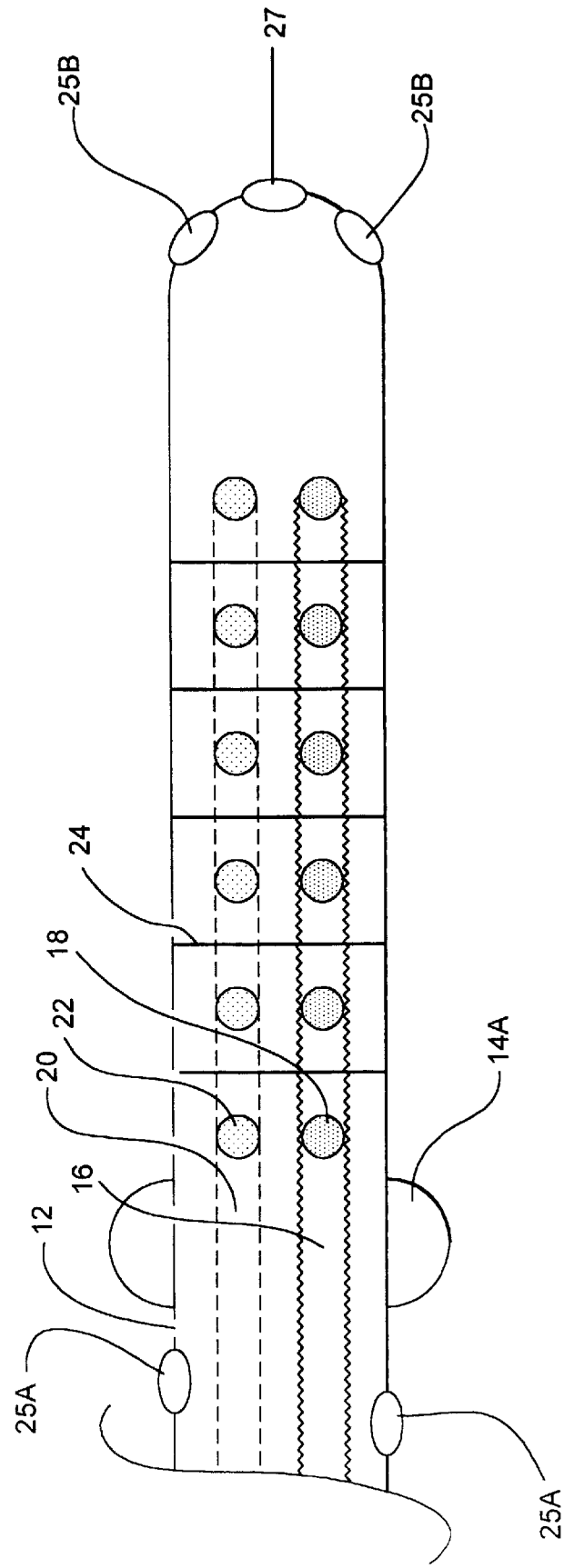
FIG. 1B illustrates a catheter with a proximal expandable member which may be used in the present invention.

FIG. 1B illustrates an alternate embodiment of a catheter with a proximal expandable member. As illustrated, the catheter includes a distal catheter body 12 with a proximal expandable member 14A for occluding a section of a body lumen proximal to a selected section of the body lumen. The catheter also includes a gene therapy composition delivery lumen 16 which terminates in one or more gene therapy composition delivery ports 18 at the distal catheter body 12. The gene therapy composition delivery ports 18 are preferably positioned relative to the expandable member 14A such that a gene therapy composition is delivered into the body lumen distal to the proximal occluded section of the body lumen. Since the body lumen is occluded, fluid in the body lumen does not wash away the gene therapy agent.

Figure 1C:
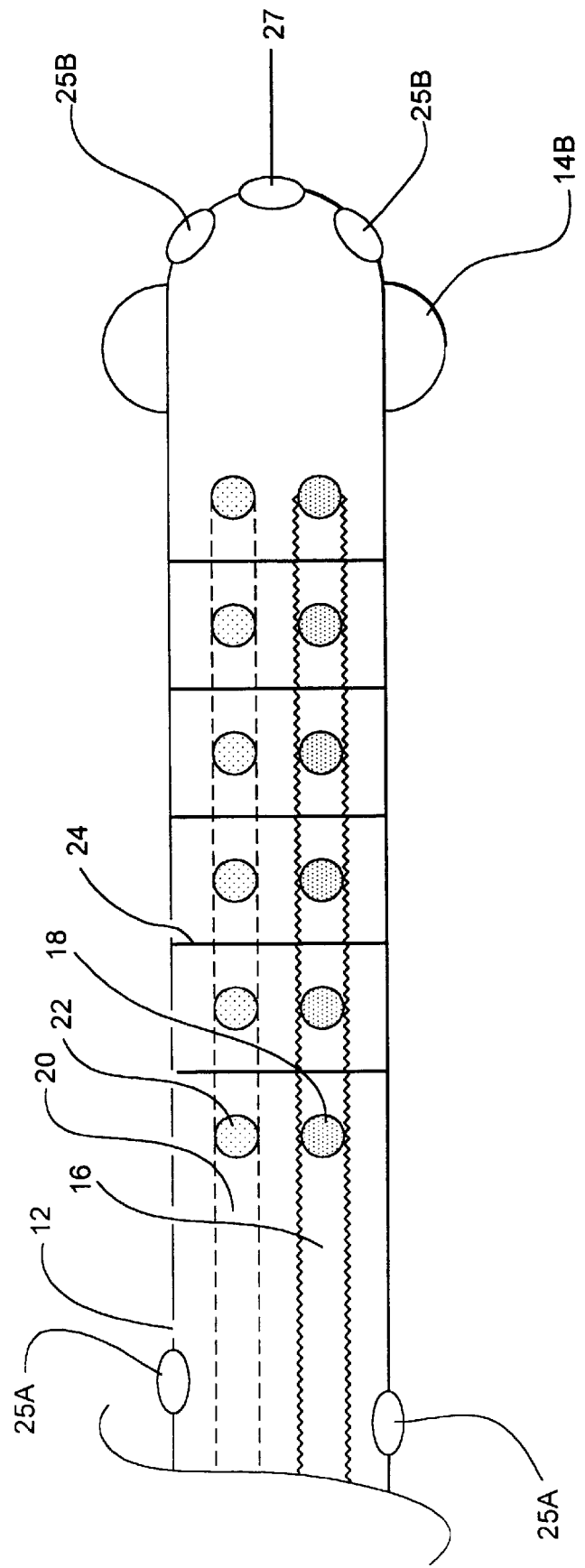
FIG. 1C illustrates a catheter with a distal expandable member which may be used in the present invention.

FIG. 1C illustrates an alternate embodiment of a catheter with a distal expandable member which may be used in the present invention. As illustrated, the catheter includes a distal catheter body 12 with a distal expandable member 14B for occluding a section of a body lumen distal to a selected section of the body lumen. The catheter also includes a gene therapy composition delivery lumen 16 which terminates in one or more gene therapy composition delivery ports 18 at the distal catheter body 12. The gene therapy composition delivery ports 18 are preferably positioned relative to the expandable member 14B such that a gene therapy composition is delivered into the body lumen proximal to the distal occluded section of the body lumen. Since the body lumen is occluded, the gene therapy composition pools adjacent the distal expandable member. Fluid in the body lumen does flow past the distal expandable member and therefore does not wash away the gene therapy agent.

FIGS. 1D–1M illustrate alternate embodiments of a catheter with an expandable member for delivering the gene therapy agent to a selected section of a body lumen. In each of these embodiments, the expandable member is positioned adjacent the selected section and expanded to deliver the gene therapy agent to the selected section.

Figure 1D:
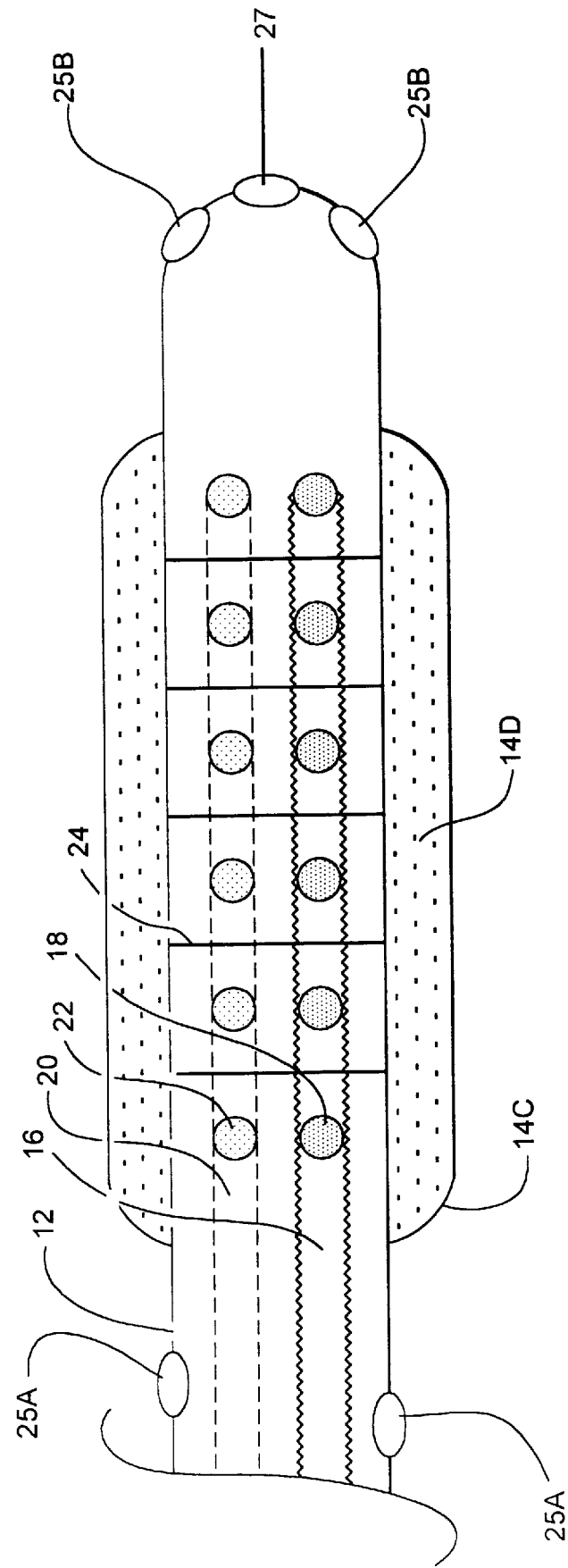
FIG. 1D illustrates a catheter with a porous membrane for delivering the gene therapy agent which may be used in the present invention.

As illustrated in FIG. 1D, the catheter may include a distal catheter body 12 with an expandable member 14C formed of a porous membrane 14D for occluding a selected section of the body lumen. The catheter also includes a gene therapy composition delivery lumen 16 which terminates in one or more gene therapy composition delivery ports 18 at the expandable member 14C and delivers the gene therapy composition through the porous membrane 14D to the selected section of the body lumen. In this embodiment, the expandable member 14C serves to localize the gene therapy composition adjacent the selected section of the body lumen. In one regard, the expandable member 14C may act like a wet sponge and keep the gene therapy composition relatively undiluted and adjacent the selected section of the body lumen.

Figure 1E:
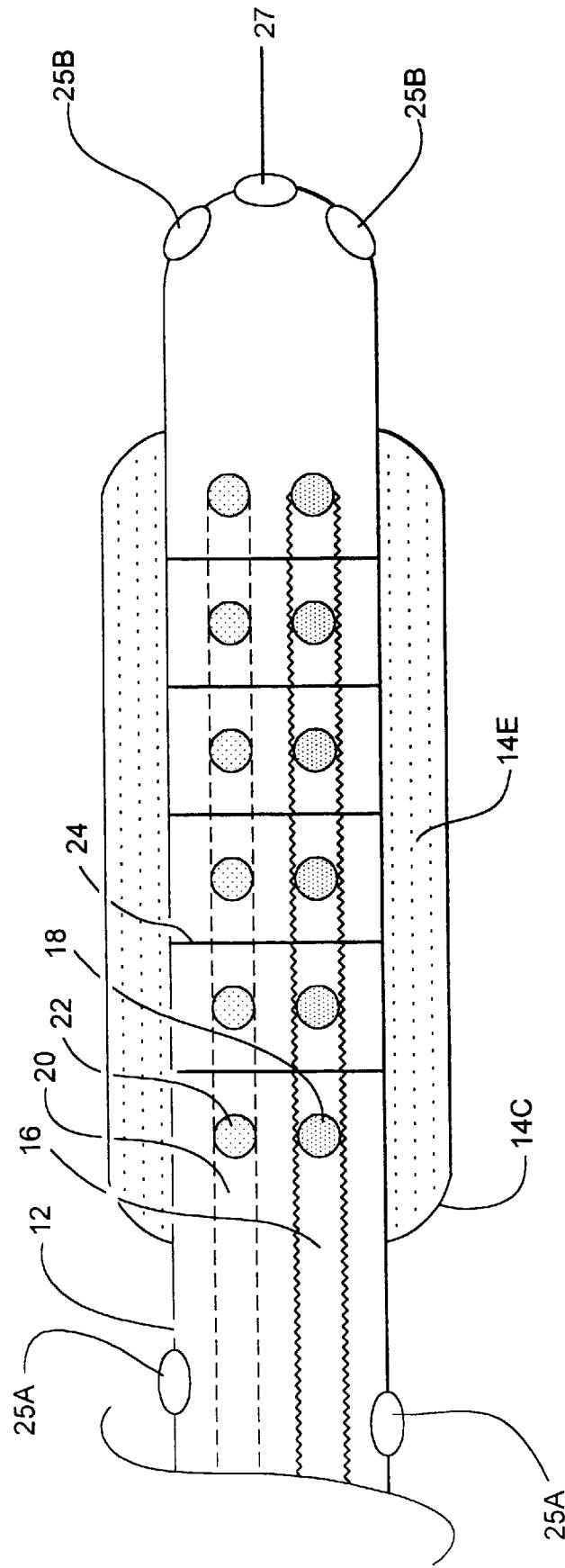
FIG. 1E illustrates a catheter with a microporous membrane for delivering the gene therapy agent which may be used in the present invention.
Figure 1F:
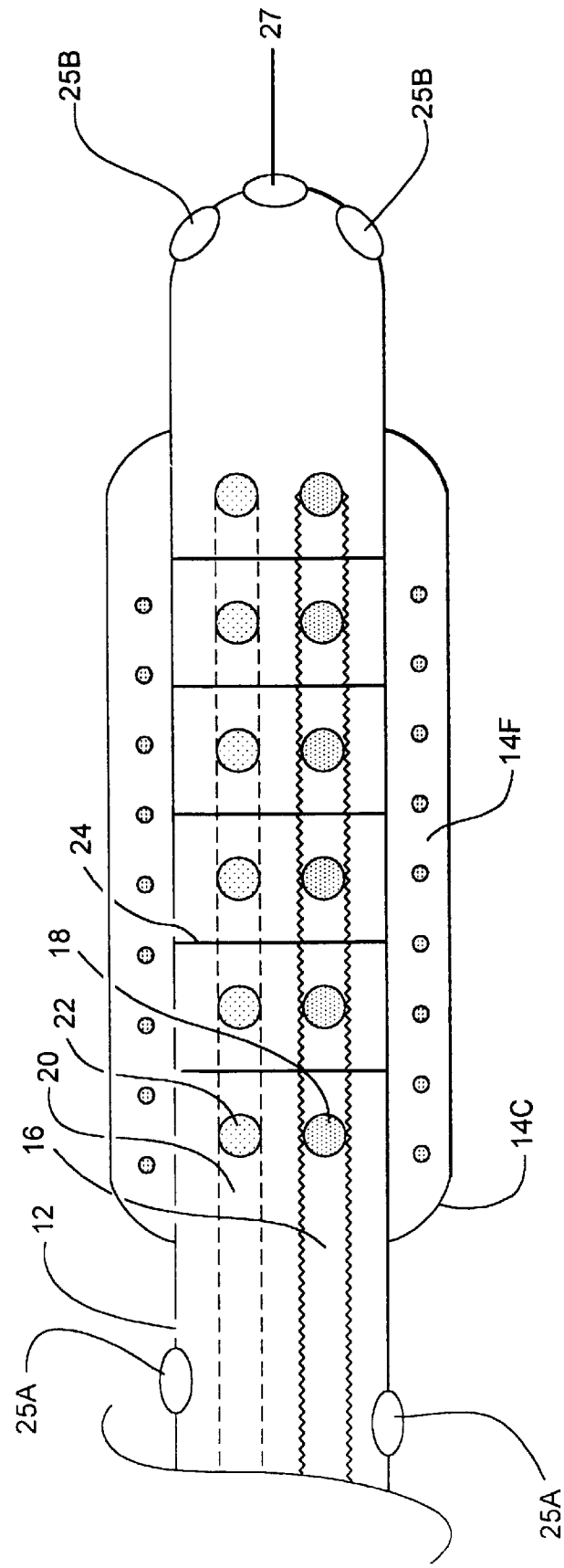
FIG. 1F illustrates a catheter with a macroporous membrane for delivering the gene therapy agent which may be used in the present invention.
Figure 1G:
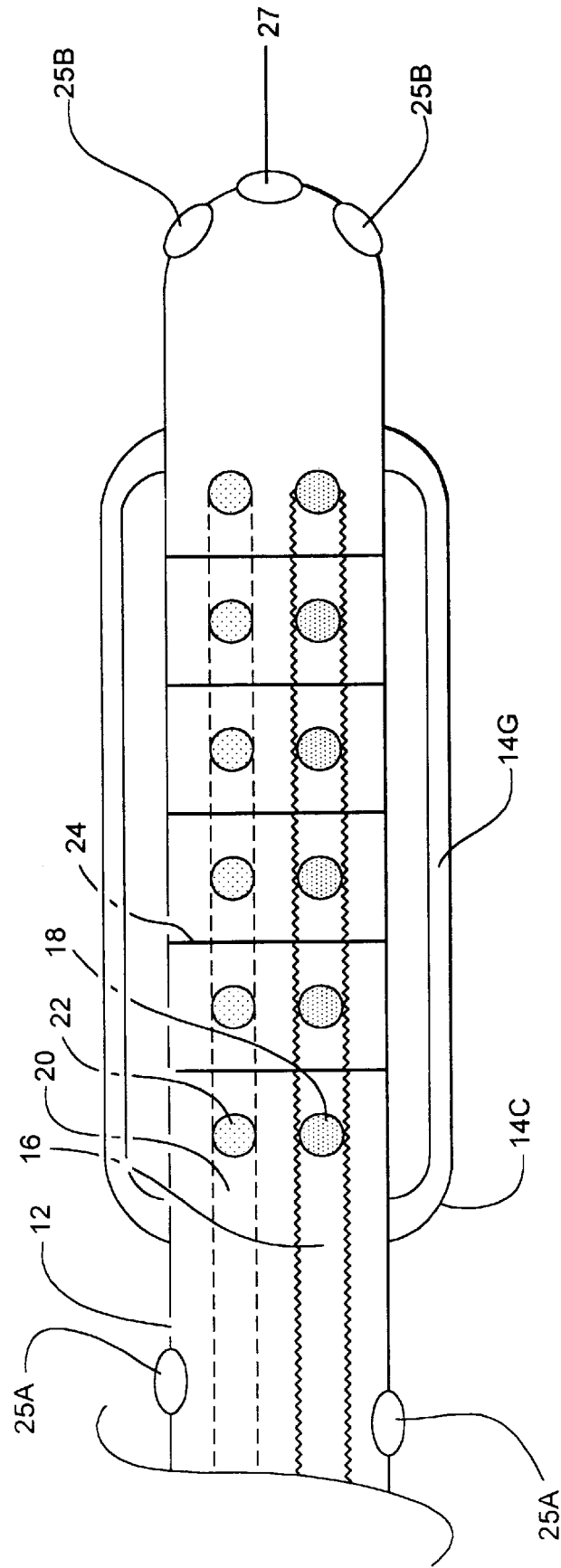
FIG. 1G illustrates a catheter with a balloon within a balloon for delivering the gene therapy agent which may be used in the present invention.
Figure 1H:
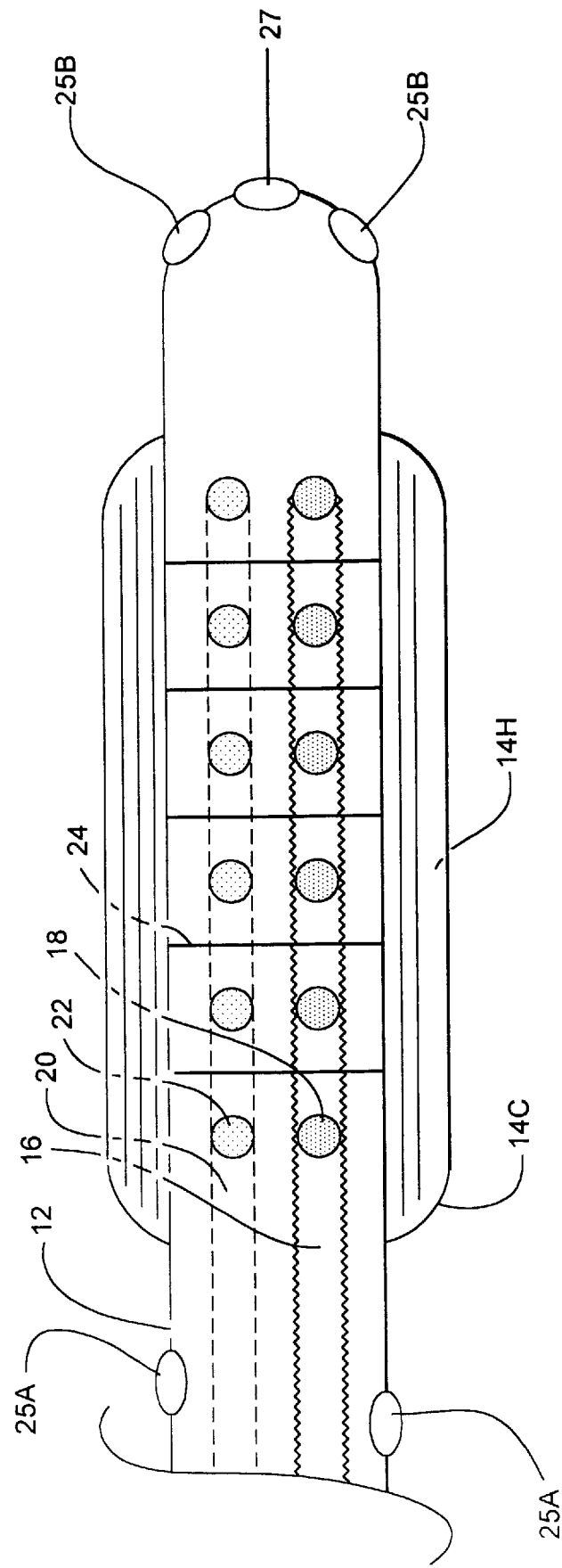
FIG. 1H illustrates a catheter with a channeled balloon for delivering the gene therapy agent which may be used in the present invention.
Figure 1I:
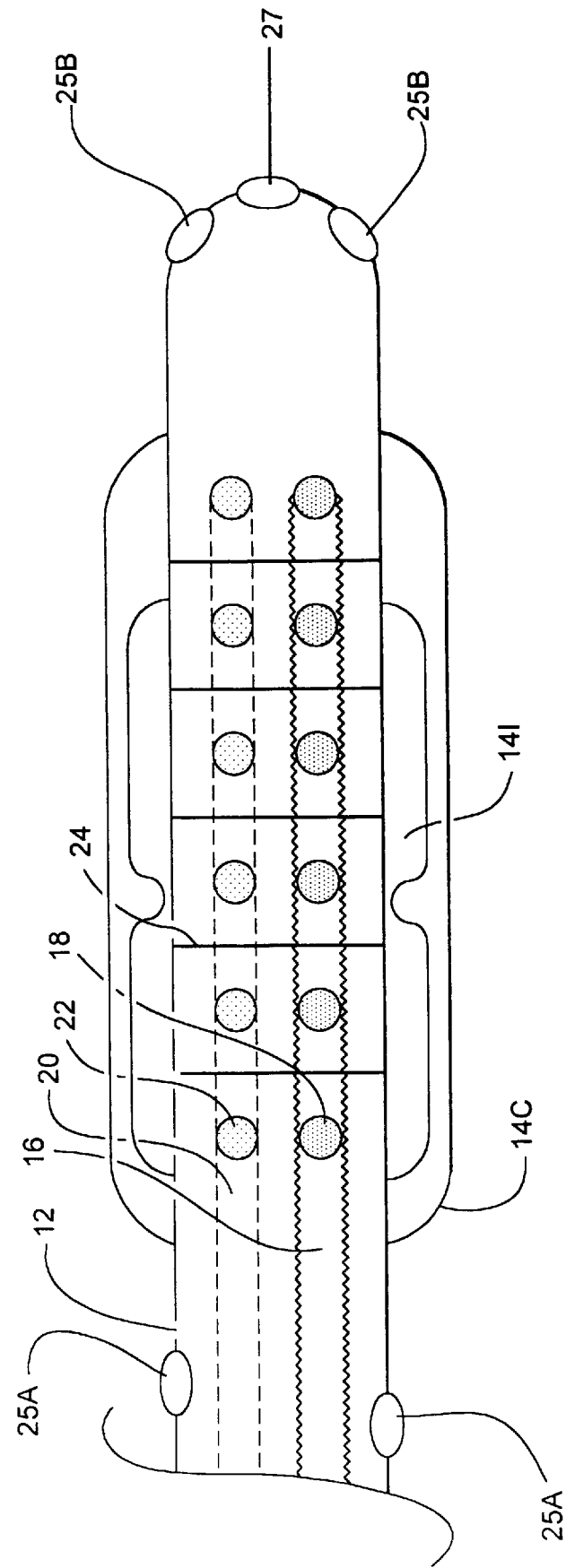
FIG. 1I illustrates a catheter with an infusion sleeve for delivering the gene therapy agent which may be used in the present invention.
Figure 1J:
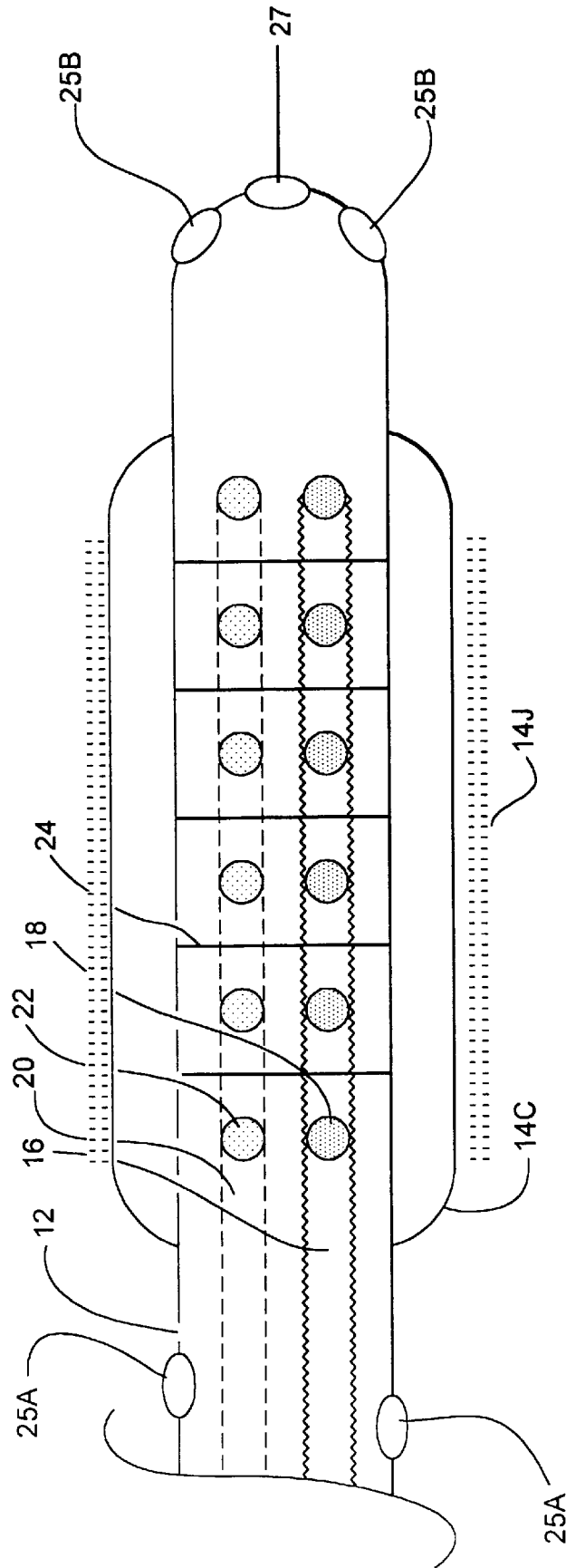
FIG. 1J illustrates a catheter with a hydrogel balloon for delivering the gene therapy agent which may be used in the present invention.
Figure 1K:
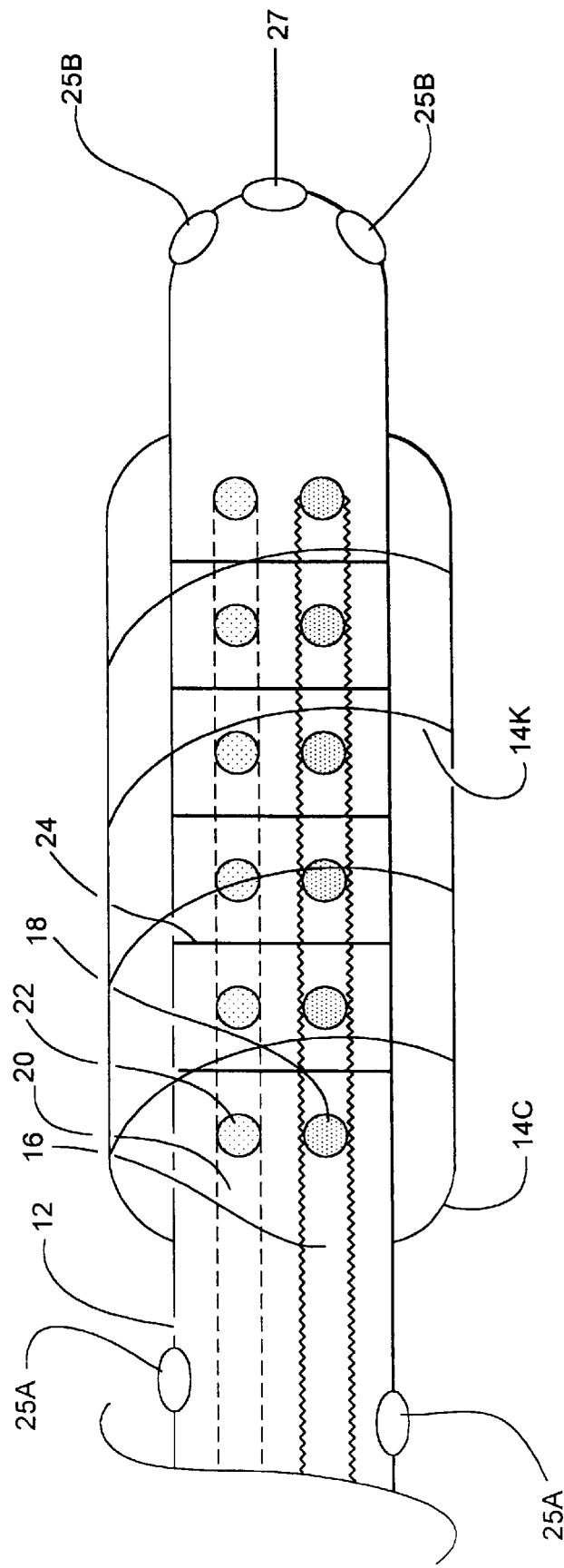
FIG. 1K illustrates a catheter with a multichambered balloon for delivering the gene therapy agent which may be used in the present invention.
Figure 1L:
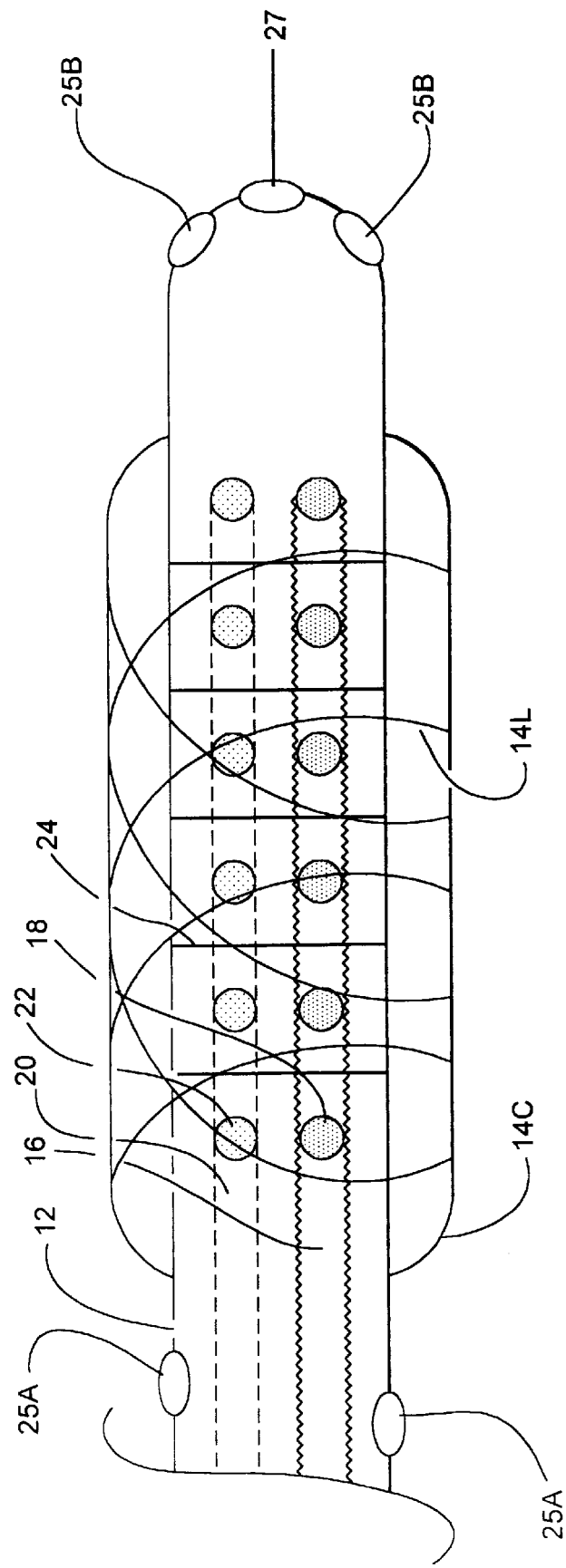
FIG. 1L illustrates a catheter with a coated stent on the outside for delivering the gene therapy agent which may be used in the present invention.

FIGS. 1E–1M illustrate alternate embodiments of a catheter with an expandable member 14C for positioning adjacent the selected section for delivering the gene therapy agent to the selected section. In FIG. 1E, the expandable member 14C includes a microporous membrane 14E. In FIG. 1F, the expandable member 14C includes a macroporous balloon 14F. In FIG. 1G, the expandable member 14C includes a balloon within a balloon 14G. In FIG. 1H, the expandable member 14C includes a channeled balloon. In FIG. 1I, the expandable member 14C includes an infusion sleeve. In FIG. 1J, the expandable member 14C includes a hydrogel balloon 14J. In FIG. 1K, the catheter includes a multichambered balloon 14K. In FIG. 1L, the catheter includes a coated stent 14L on the outside of the expandable member 14C.

In each of the above embodiments which include an expandable member for occluding the selected section, the expandable member may optionally include a plurality of projections extending from the surface of the expandable member. These projections may be used to disrupt the surface of the body lumen at the selected section and facilitate the entry of the gene therapy agent into cells and tissue at the selected section. Optionally, the plurality of projections may be in the form of needles with a lumen for delivering the gene therapy agent into the tissue. These projections, optionally in the form of needles, preferably have a length as short as a several microns to a length of a few millimeters.

Figure 1M:
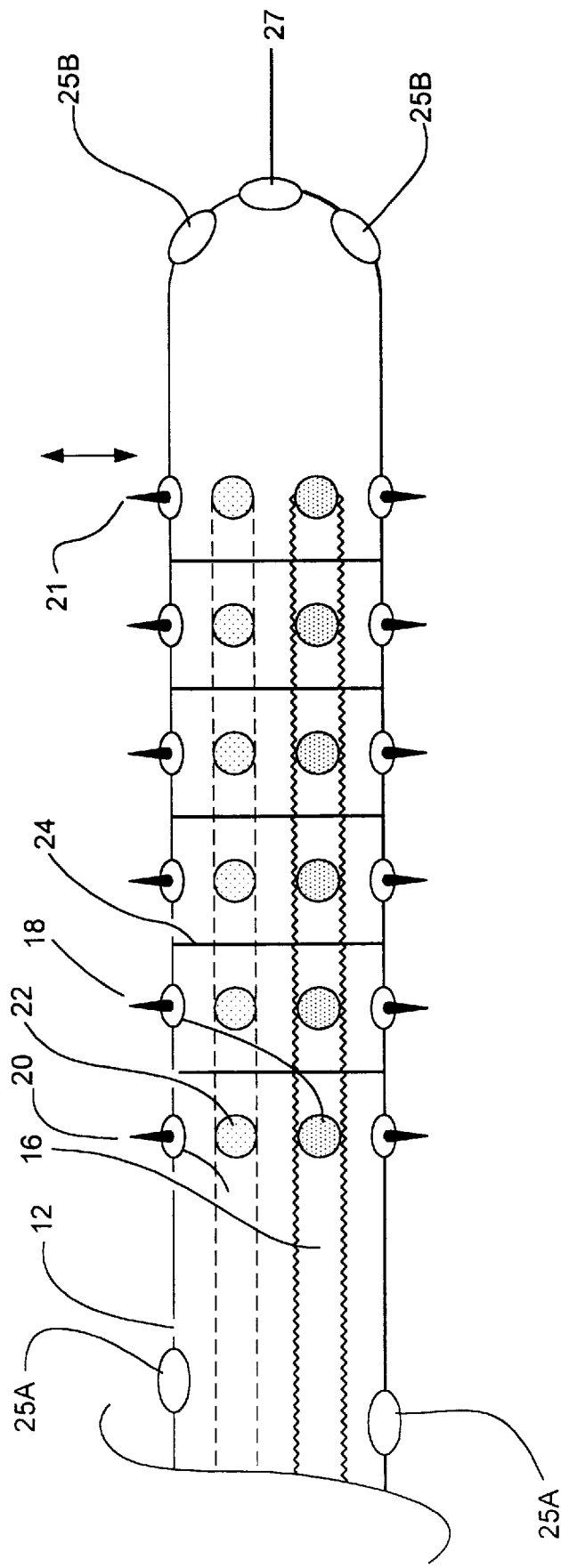
FIG. 1M illustrates a catheter with one or more injection needles through which the gene therapy agent may be delivered into the selected section of the body lumen.

FIG. 1M illustrates an alternate embodiment of a catheter with one or more injection needles through which the gene therapy agent may be delivered into the selected section of the body lumen. As illustrated, the catheter includes a distal catheter body 12 with one or more injection needles 21 which are extendable and retractable relative to the distal catheter body. The catheter also includes a gene therapy composition delivery lumen 16 which terminates into the one or more injection needles 21 which are used to deliver the gene therapy composition into the selected section of the body lumen. In this embodiment, the injection needles provide localized delivery of the gene therapy composition into the selected section of the body lumen. Ultrasound is then used to facilitate entry of the gene therapy composition into cells within the selected section.

In regard to each of the above catheter embodiments, the catheter may include a wash lumen 20 which terminates in one or more washing ports 22 at the distal catheter body 12. The washing ports 22 are preferably positioned relative to the catheter such that a washing fluid, such as saline or a microbubble booster, may be delivered into the body lumen to wash the selected section of the body lumen. The washing fluid can be used to wash the selected section of the body lumen prior to delivery of the gene therapy composition, for example to remove blood from the selected section. The washing fluid can also be used to wash the selected section of the body lumen after delivery of the gene therapy composition in order to remove non-absorbed gene therapy composition from the selected section of the body lumen. Ultrasound energy is optionally delivered during the washing step(s).

Each of the above catheter embodiments may also include a bypass lumen with entry 25A and exit 25B ports which allow fluid to pass through the body lumen while the body lumen is occluded by mechanisms of the catheter. Each of the above embodiments can also include a guidewire lumen for use with a guidewire 27 to navigate the catheter body in the body lumen.

In regard to each of the above catheter embodiments, ultrasound energy can be generated at an ultrasound energy source located external to the body and transmitted via wire to the ultrasound elements 24. Ultrasound can also be internally generated from electrical power delivered to the ultrasound elements 24 from an electrical energy source. A suitable example of an ultrasound element for internal generation of ultrasound energy is a piezoelectric ceramic oscillator. The ultrasound elements can be shaped as a cylinder, a hollow cylinder and a disk which are concentric with the catheter. The ultrasound elements can also be an array of smaller ultrasound elements or a thin plate positioned within the body of the catheter. Similarly, a single ultrasound element can be composed of several smaller ultrasound elements.

An active length of catheter is defined by the number and spacing of the ultrasound elements and gene therapy composition delivery ports at the distal end. The number of ultrasound elements depends on the length of the vessel being treated. Suitable numbers of ultrasound elements include, but are not limited to 2–10, 2–8 and 4–6. Each of the ultrasound elements can be from one millimeter in length to up to a half centimeter in length. Other dimensions can also be used. The spacing between ultrasound elements can be approximately equal to the length of each ultrasound element. If one ultrasound element has a length L, a second ultrasound element can be spaced up to three L lengths away from the first ultrasound element. Suitable L include, but are not limited to 0.2–2 cm, 0.2–1.2 cm and 0.3–0.7 cm.

The ultrasound elements can be positioned internally or externally to catheter, and can have any number of different geometric designs. Suitable, geometric designs include, but are not limited to a band which lies flush with the circumference of the catheter. Additionally, ultrasound elements can be designed provide any desired directionality of ultrasound.

The ultrasound delivered by the catheter to the selected region of the body lumen preferably has a frequency between about 20 KHz to several MHz, more preferably between about 100 KHz and 1.5 MHz. The ultrasound transducer also preferably produces an ultrasound signal with an intensity of between about 0.1 MPa and 20 MPa, more preferably between about 5 MPa and 15 MPa. The ultrasound also preferably has an acoustic power of between about 0.2 watts and 20 watts, more preferably between about 0.6 watts and 2 watts.

Figure 1N:
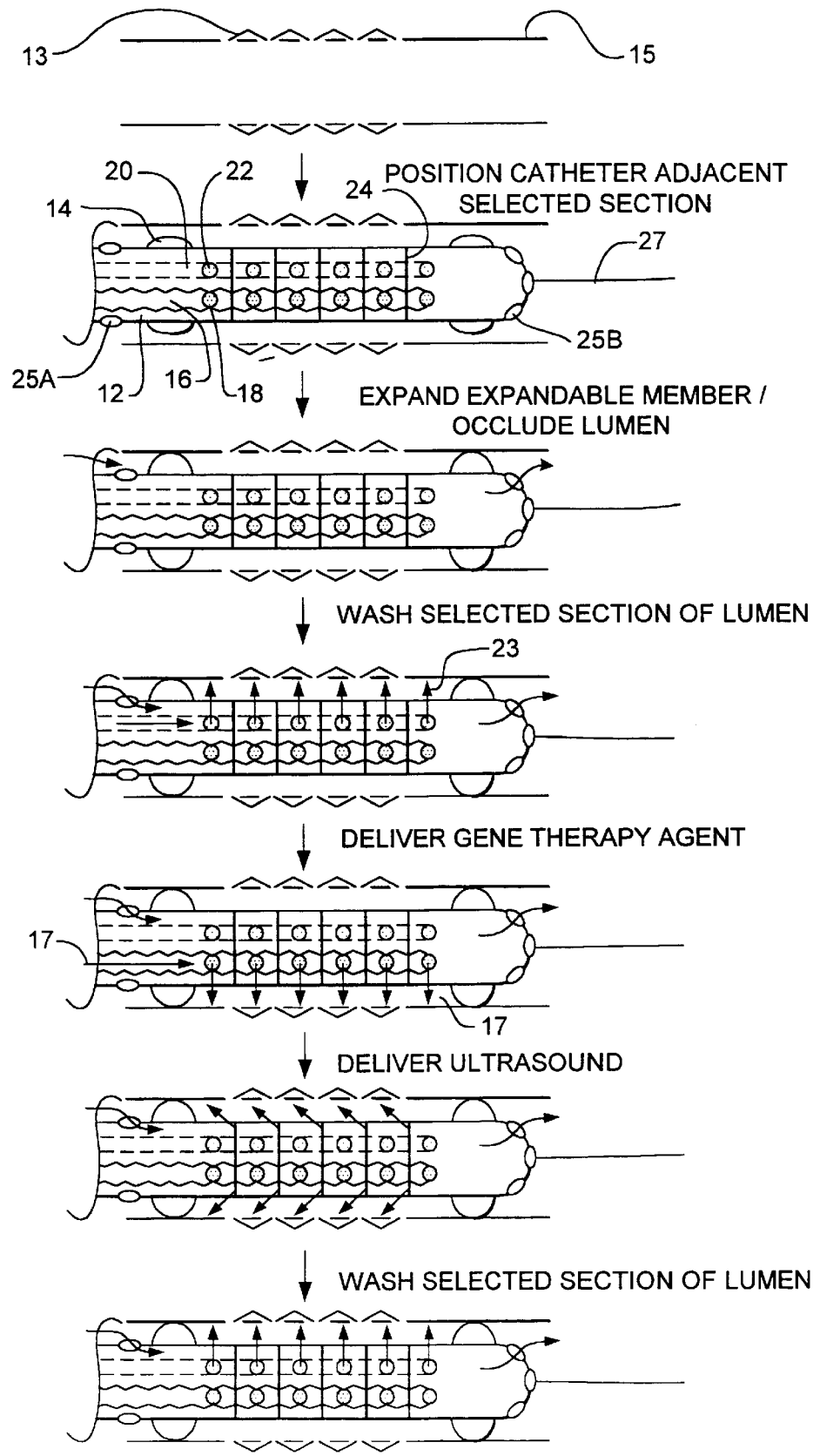
FIG. 1N illustrates a method of gene therapy using the catheter illustrated in FIG. 1A.
Figure 10:
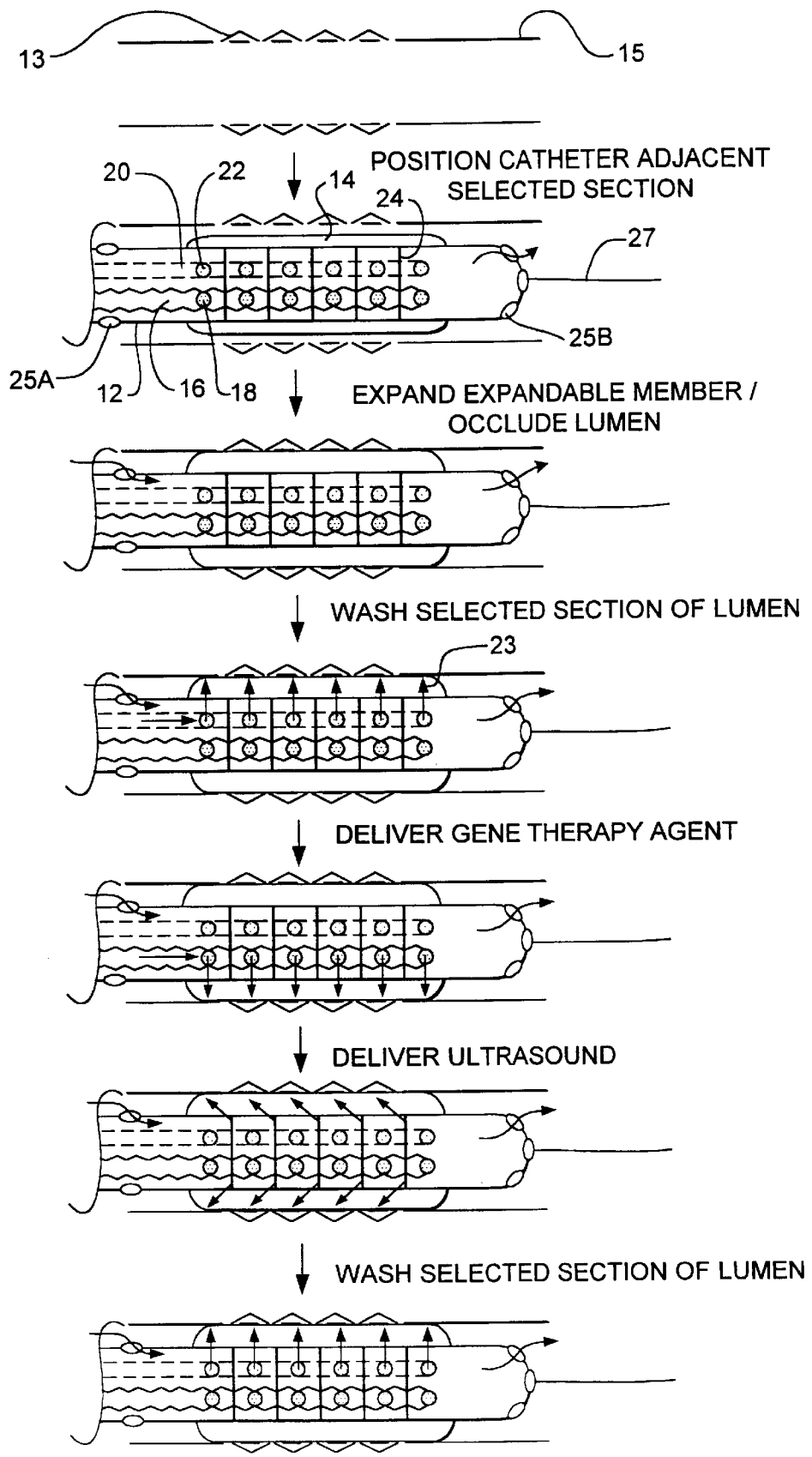

5. Methods For Delivering Gene Therapy Agent To Selected Region Of A Body Lumen Methods are also provided for performing gene therapy on a selected section of a body lumen. FIG. 1N illustrates a particular embodiment of the method which utilizes a catheter such as the one illustrated in FIG. 1A. According to the method, a distal catheter body 12 is placed in a selected section 13 of a body lumen 15 such that expandable members 14A, 14B on the catheter are proximal and distal to the selected section 13 of the body lumen 15. The expandable members 14A, 14B are expanded in order to occlude the body lumen 15. A gene therapy composition 17 is then delivered into the selected section 13 of the body lumen 15. Ultrasound energy 19 is then delivered for a period of time, the ultrasound facilitating the entry of gene therapy agents in the composition to enter into the cells. As illustrated in FIG. 1N, the method may optionally also include the step of washing the selected section 13 of the body lumen 15, for example by delivering and removing saline 23, prior to delivering the gene therapy composition 17. The method may also optionally include the step of washing the selected section 13 of the body lumen 15, for example by delivering and removing saline 23, after delivering the gene therapy composition 17. This prevents the gene therapy agent from transfecting cells outside the region. Ultrasound energy may be delivered during one or both of the washing steps, optionally in the presence of a microbubble booster. It is believed that the use of ultrasound energy during the washing step prior to delivery of the gene therapy composition pretreats the body lumen for the entry of the gene therapy composition into cells of the body lumen.

FIG. 1O illustrates another embodiment of the method which utilizes a catheter such as the ones illustrated in FIGS. 1D–1M. For sake of illustration, the catheter of FIG. 1D is shown although other types of catheters may be readily substituted. According to the method, a distal catheter body 12 is placed in a selected section 13 of a body lumen 15 such that the expandable member 14C on the catheter is opposed to the selected section 13 of the body lumen 15. The expandable member 14C is expanded in order to occlude the body lumen 15 and place the porous membrane 14D in contact with the selected section 13 of the body lumen 15. A gene therapy composition 17 is then delivered through the expandable member into the selected section 13 of the body lumen 15. Ultrasound energy 19 is then delivered for a period of time, the ultrasound facilitating the entry of gene therapy agents in the composition to enter into the cells. As illustrated in FIG. 1O, the method may optionally also include the step of washing the selected section 13 of the body lumen 15, for example by delivering and removing saline 23, prior to delivering the gene therapy composition 17. The method may also optionally include the step of washing the selected section 13 of the body lumen 15, for example by delivering and removing saline 23, after delivering the gene therapy composition 17. Ultrasound energy may be delivered during one or both of the washing steps, optionally in the presence of a microbubble booster.

Figure 1P:
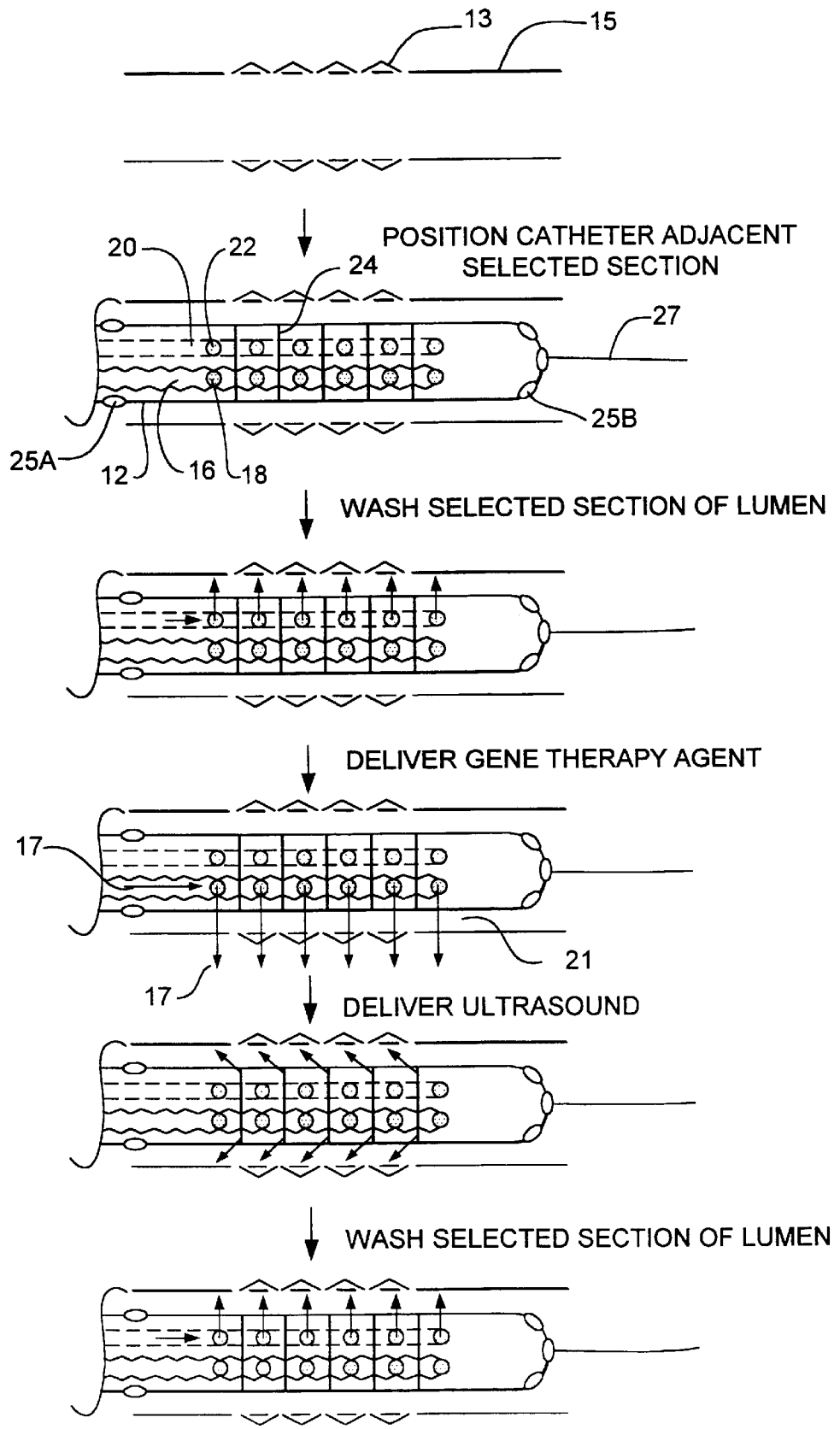
FIG. 1P illustrates another embodiment of the method which utilizes a catheter such as the one illustrated in FIG. 1M which includes injection needles.

FIG. 1P illustrates another embodiment of the method which utilizes a catheter such as the one illustrated in FIG. 1M which includes injection needles. According to the method, a distal catheter body 12 is placed in a selected section 13 of a body lumen 15 such that the one or more injection needles 21 are opposed to the selected section 13 of the body lumen 15. The one or more injection needles 21 are then extended from the catheter into the selected section 13 of the body lumen 15. A gene therapy composition 17 is then delivered through the needles into the selected section 13 of the body lumen 15. Ultrasound energy 19 is then delivered for a period of time, the ultrasound facilitating the entry of gene therapy agents in the composition to enter into the cells. As illustrated in FIG. 1P, the method may optionally also include the step of washing the selected section 13 of the body lumen 15, for example by delivering and removing saline 23, prior to delivering the gene therapy composition 17. The method may also optionally include the step of washing the selected section 13 of the body lumen 15, for example by delivering and removing saline 23, after delivering the gene therapy composition 17. Ultrasound energy may be delivered during one or both of the washing steps, optionally in the presence of a microbubble booster.

Although the steps of delivering the gene therapy composition and applying ultrasound energy are illustrated in FIGS. 1N–1P as being separate, it is noted that ultrasound energy may be delivered before, during, and/or after the gene therapy composition. In one particular embodiment, ultrasound energy is delivered intermittently as multiple boluses of gene therapy composition are delivered. As used here, intermittent delivery refers to ultrasound being delivered for a first period of time, being not delivered for a second period of time, and then being delivered for a third period of time, the second period of time having a duration of at least 0.1 second, preferably at least 0.5 second, more preferably at least 1 second, and most preferably at least 3 seconds. Functionally, ultrasound is delivered intermittently in order to allow additional gene therapy composition, preferably including microbubbles, to be delivered to cells to be treated during a period of time when no ultrasound is applied. Ultrasound causes microbubbles in the composition to burst. Accordingly, by intermittently delivering ultrasound, it is possible to deliver a composition with microbubbles when no ultrasound is delivered so that the microbubbles can act adjacent the cells to be treated instead of being burst prior to reaching the cells.

6. Catheter With Plural Ultrasound Elements For Delivering Gene Therapy Agent To Selected Section Of A Body Lumen FIG. 2A illustrates another embodiment of an ultrasound catheter 30 which may be used in the present invention. In this embodiment, the catheter includes a plurality of ultrasound elements 32, temperature sensors 33 and gene therapy agent delivery ports 34 positioned along a selected section of the catheter 30. The catheter 30 also includes a guidewire lumen 35 which can accommodate a guidewire 36. At least one gene therapy composition delivery port 34 is correlated with each ultrasound element 32. Discrete ultrasound elements 32 are used in this embodiment instead of one continuous ultrasound element, as illustrated in FIGS. 1A–1E. Although the catheter illustrated in FIG. 2A has two expandable members 31A, 31B similar to the catheter illustrated in FIG. 1A, it is noted that the catheter may alternatively have only one expandable member or may have a membrane or injection needles as illustrated in FIGS. 1B–1E.

Catheters introduced through circulatory vessels must be flexible in order to reach a desired location where the lesion 38 is located. When a large lesion is present, a single ultrasound element which is long enough to deliver ultrasound energy the length of the lesion reduces the flexibility of the catheter 30. Therefore, multiple segmented ultrasound elements 32 provide an increased flexibility over a long single element.

The average power required to activate an ultrasound element 32 is proportional to the activated area of the ultrasound element 32. Hence, a 2-cm long element requires approximately twice as much power as a 1-cm long element of similar shape and diameter. As the power increases, the diameter of the electrical wires that bring electrical energy to the ultrasound elements 32 must also increase. This requires an increase in catheter diameter that in turn reduces flexibility and restricts use of the catheter 10 in larger vessels.

These difficulties are solved by the catheter illustrates in this embodiment that creates a distribution of smaller ultrasound elements 32. The ultrasound elements 32 are sized small enough so that they in combination with the catheter 30 provide a flexible structure that can be moved down a tortuous vein tree to the site of the lesion or to any vessel in which there is a lengthy lesion to be treated. Additionally, the ultrasound elements 32 are small enough that each individual ultrasound element 32, if excited individually, does not take an inordinate amount of power through the wires which supply power to the catheter 30. The ultrasound elements 32 are positioned to reduce dead space between the ultrasound elements 32. This provides some overlap in the radiation patterns that emit from each of the ultrasound elements 32 to maximize the enhancement effect. There is also a proximity between the ultrasound element 32 and the gene therapy agent delivery ports 34 so that the drug emitted proximal or next to the catheter 30 is then affected by a nearby source of ultrasound energy. However, the drug delivery ports 34 do not need to be correlated with a particular ultrasound element 32 and there need be no relationship between the number of drug delivery ports 34 and the number of ultrasound elements 32.

Figure 3A:
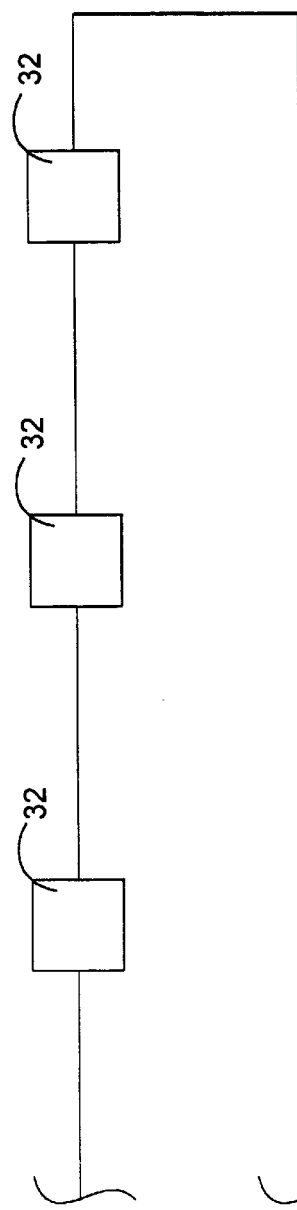
FIG. 3A illustrates ultrasound elements connected in series.
Figure 3B:
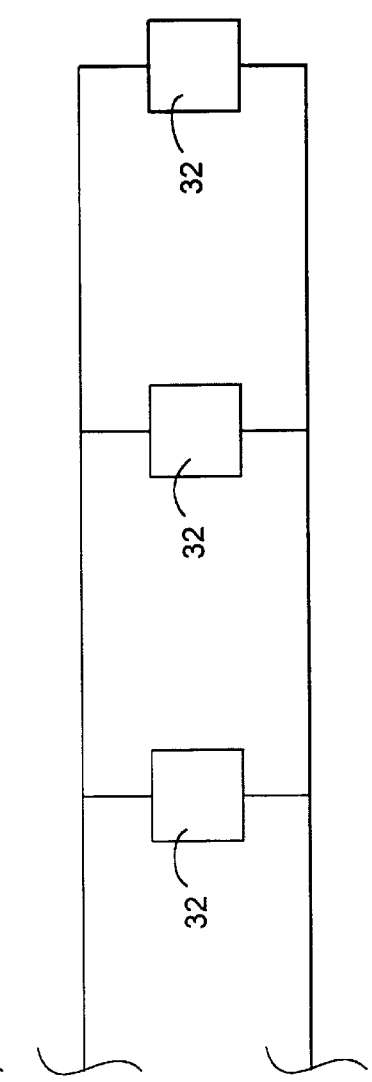
FIG. 3B illustrates ultrasound elements connected in-parallel.

The individual ultrasound elements 32 can each be individually powered. When the catheter includes N ultrasound elements, the catheter body must include 2N wires to individually power N ultrasound elements 32. The individual ultrasound elements 32 can also be electrically coupled in serial or in parallel as illustrated in FIGS. 3A and 3B. These arrangements permit maximum flexibility as they require only 2N wires. Each of the ultrasound elements receives power simultaneously whether the ultrasound elements are in series or in parallel. When the ultrasound elements 32 are in series, less current is required to produce the same power from each ultrasound element 32 than when the ultrasound elements 32 are connected in parallel. The reduced current allows smaller wires to be used to provide power to the ultrasound elements 32 and accordingly increases the flexibility of the catheter 30. When the ultrasound elements 32 are connected in parallel, an ultrasound element 32 can break down and the remaining ultrasound elements 32 will continue to operate.

Figure 3C:
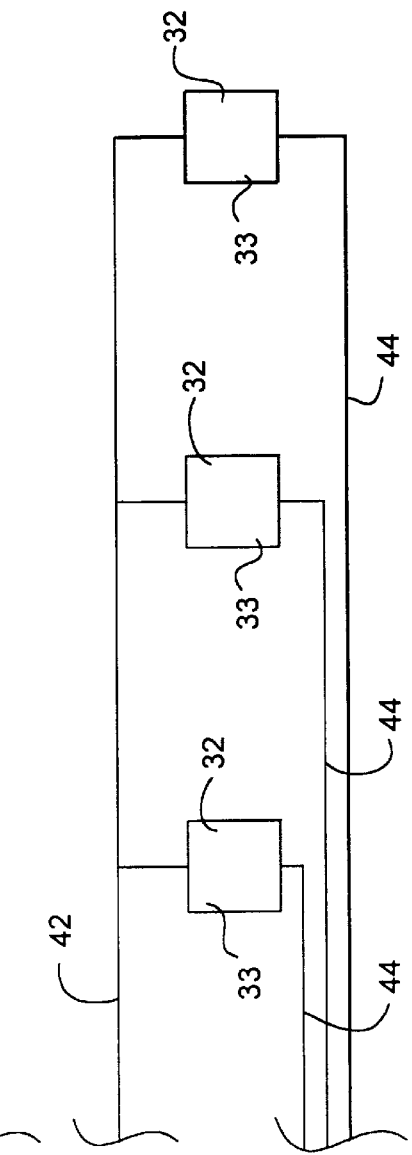
FIG. 3C illustrates ultrasound elements or temperature sensors connected through a common wire.

As illustrated in FIG. 3C, a common wire 42 can provide power to each of the ultrasound elements 32 while each ultrasound element 32 has its own return wire 44. A particular ultrasound elements 32 can be individually activated by closing a switch (not shown) to complete a circuit between the common wire 42 and the particular ultrasound element's return wire 44. Accordingly, a catheter with N ultrasound elements requires only N+1 wires and still permits independent control of the ultrasound elements 32. This reduced number of wires increases the flexibility of the catheter 30. To improve the flexibility of the catheter, the individual return wires can have diameters which are smaller than the common wire diameter. For instance, in an embodiment where N ultrasound elements will be powered simultaneously, the diameter of the individual wires can be the square root of N times smaller than the diameter of the common wire.

Figure 2:
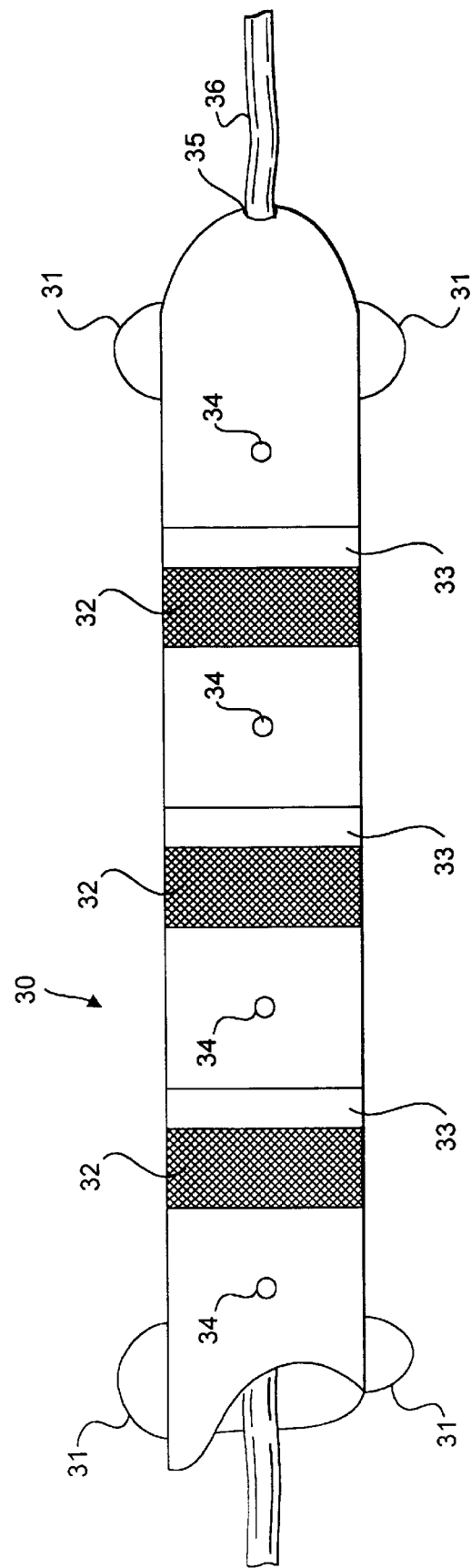
FIG. 2 is a sideview of a catheter with segmented ultrasound elements.

As illustrated in FIG. 2, a temperature sensor 33 may be positioned adjacent each ultrasound element 32. Suitable temperature sensors 33 include, but are not limited to, thermistors, thermocouples and resistance temperature detectors, RTDs, and fiber optic temperature sensors which use thermalchromic liquid crystals. Suitable temperature sensor 33 geometries include, but are not limited to, a point, patch, stripe and a band around the catheter 30 as illustrated. The temperature sensors 33 can be positioned on the catheter 30, on the ultrasound element and adjacent the ultrasound elements 32 as illustrated.

The temperature sensors 33 can be electrically connected as illustrated in FIG. 3C. Each temperature sensor 33 can be coupled with a common wire 42 and then include its own return wire 44. Accordingly, N+1 wires can be used to independently sense the temperature at the temperature sensors 33 of a catheter 10 having N temperature sensors 33. A suitable common wire 42 can be constructed from Constantine and suitable return 44 wires can be constructed from copper. The temperature at a particular temperature sensor 33 can be determined by closing a switch (not shown) to complete a circuit between the thermocouple's return wire 44 and the common wire 42. When the temperature sensors 33 are thermocouples, the temperature can be calculated form the voltage in the circuit. To improve the flexibility of the catheter, the individual return wires can have diameters which are smaller than the common wire diameter.

Each temperature sensor 33 can also be independently wired. A catheter 30 including N temperature sensors 33 which are independently wired will require 2N wires to pass the length of the catheter.

The catheter flexibility can also be improved by using fiber optic based temperature sensors. The flexibility can be improved because only N fiber optics need to be included in the catheter to sense the temperature at N temperature sensors.

The temperature sensors 33 do not need to be correlated with the ultrasound elements 32. For instance, the catheter 30 can include a temperature sensor 33 which is positioned to provide a signal indicating the temperature of the portion of the lumen being treated. For instance, the temperature sensor 33 can be positioned between the central two ultrasound elements. The ultrasound output from the ultrasound elements 32 can be manually or automatically adjusted in response to the signal from the temperature sensor 33.

Figure 4A:
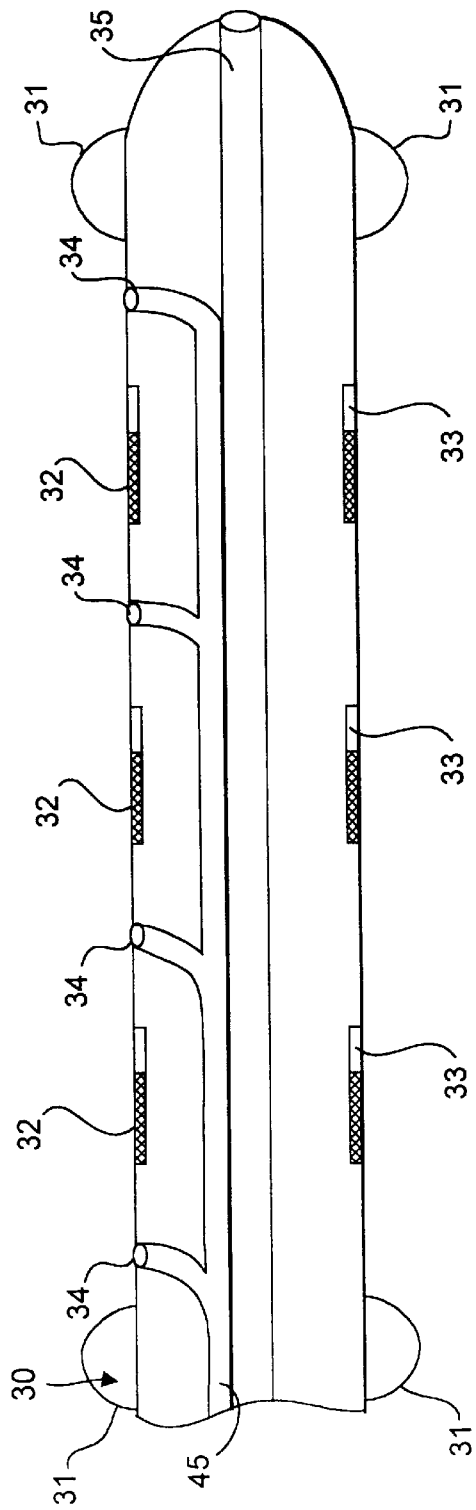
FIG. 4A is a cross section of a catheter with a lumen coupled with gene therapy composition delivery ports which are each correlated with an ultrasound element.
Figure 4B:
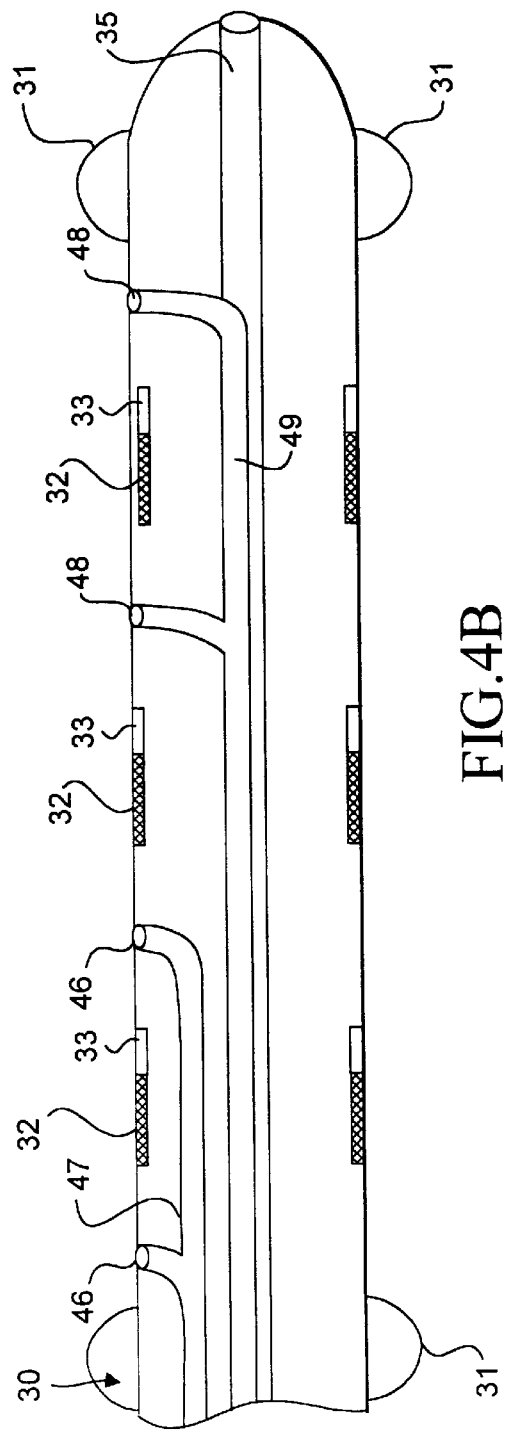
FIG. 4B is a cross section of a catheter with a first lumen for delivering drug through first gene therapy composition delivery ports.

The gene therapy composition delivery ports 34 can be coupled with a common lumen 45 as illustrated in FIG. 4A. The gene therapy composition delivery ports 34 can be positioned on one side of the catheter 30 or distributed about the surface of the catheter 30 to provide a more even delivery of the gene therapy composition. The gene therapy composition can be delivered through the common lumen 45 to the various gene therapy composition delivery ports 34 next to each of the ultrasound elements 32 so that all of the gene therapy composition delivery ports 34 deliver gene therapy composition at the same time. As illustrated in FIG. 4B, one or more gene therapy composition delivery ports 46 can be coupled with a first lumen 47 and one or more second gene therapy composition delivery ports 48 can be coupled with a second lumen 49. Accordingly, different gene therapy compositions can be delivered adjacent different ultrasound elements 32. Further, different amounts of the same gene therapy composition can be delivered adjacent particular ultrasound elements 32. As a result, the amount of gene therapy composition delivery can be adjusted to match the amount of therapeutic treatment required by a particular section of the lesion 38. Use of the ultrasound elements 32 and a plurality of drug delivery ports 34 can provide controllability and selectability of lesion modification/ destruction.

Figure 5A:
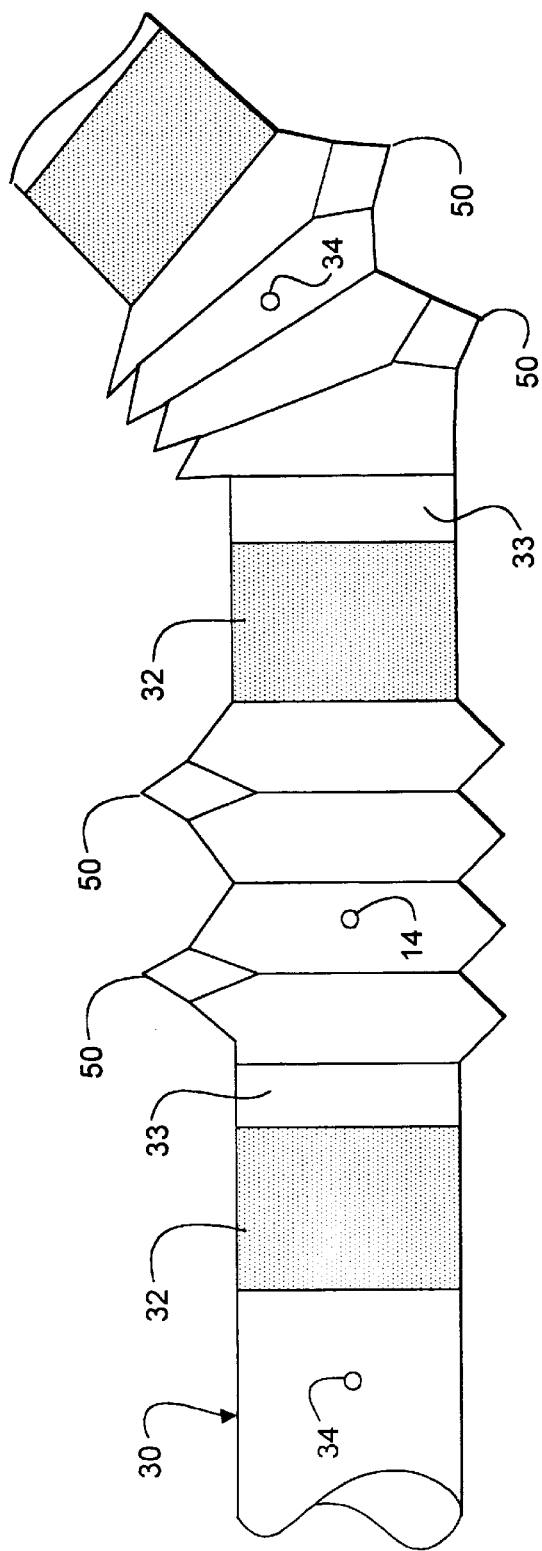
FIG. 5A is a sideview of a catheter including ribs between ultrasound elements.
Figure 5C:
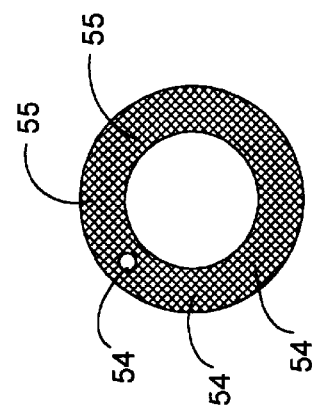
FIG. 5C is a cross section of the catheter of FIG. 5B.
Figure 5B:
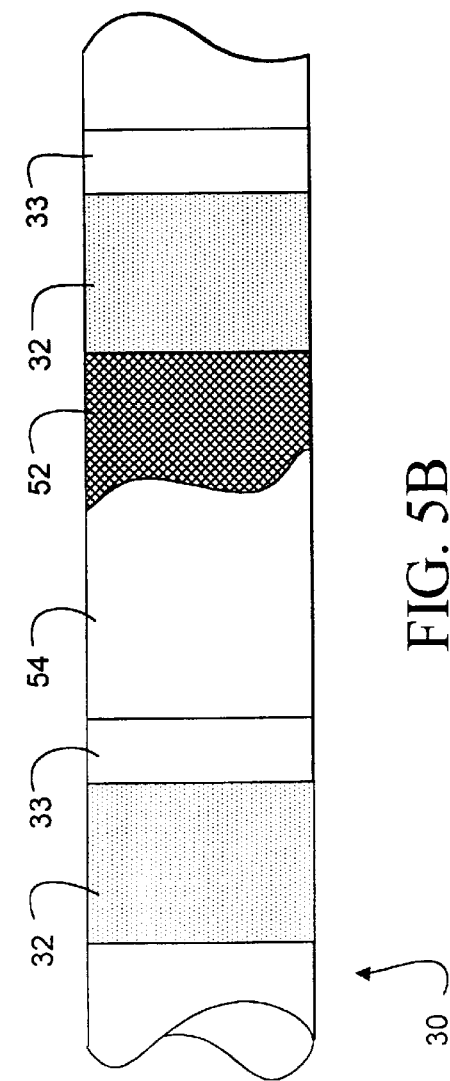
FIG. 5B is a cut-away view a catheter including webbing or mesh between the ultrasound elements.

The catheter 30 can be constructed to overcome the reduced flexibility which results from the multiple ultrasound elements 32. As illustrated in FIG. 5A, the catheter 30 can include ribs 50 between the ultrasound elements 32. The ribs 50 increase the bendability of the catheter at the ribbed locations while providing kink resistance. The added flexibility can be necessary to work the catheter 10 through tortuous vessels. As illustrated in FIG. 5B additional flexibility can be obtained by manufacturing at least the portion of the catheter 30 between the ultrasound elements 32 from a mesh 62 or braided material. As illustrated in FIG. 5C, the outer surface of the catheter 30 and the lumens within the catheter 30 are smooth 54. The smooth surfaces 54 aid in passing the catheter 30 through the body lumen and in passing fluids through the lumen. Any wires 55 present in the catheter 30 can pass through the mesh portion of the catheter 30 for additional flexibility. Suitable materials for the catheter include, but are not limited to polyolefins and polyimides and other low acoustic impedance materials. Low acoustic impedance materials are materials which readily transmit ultrasound energy with minimal absorption of the energy. Suitable materials for the mesh or braid include, but are not limited to Kevlar, stainless steel, polyetheretherketone or PEEK. Cotton braided with polymer can also serve to provide flexibility and kink resistance.

Figure 6:
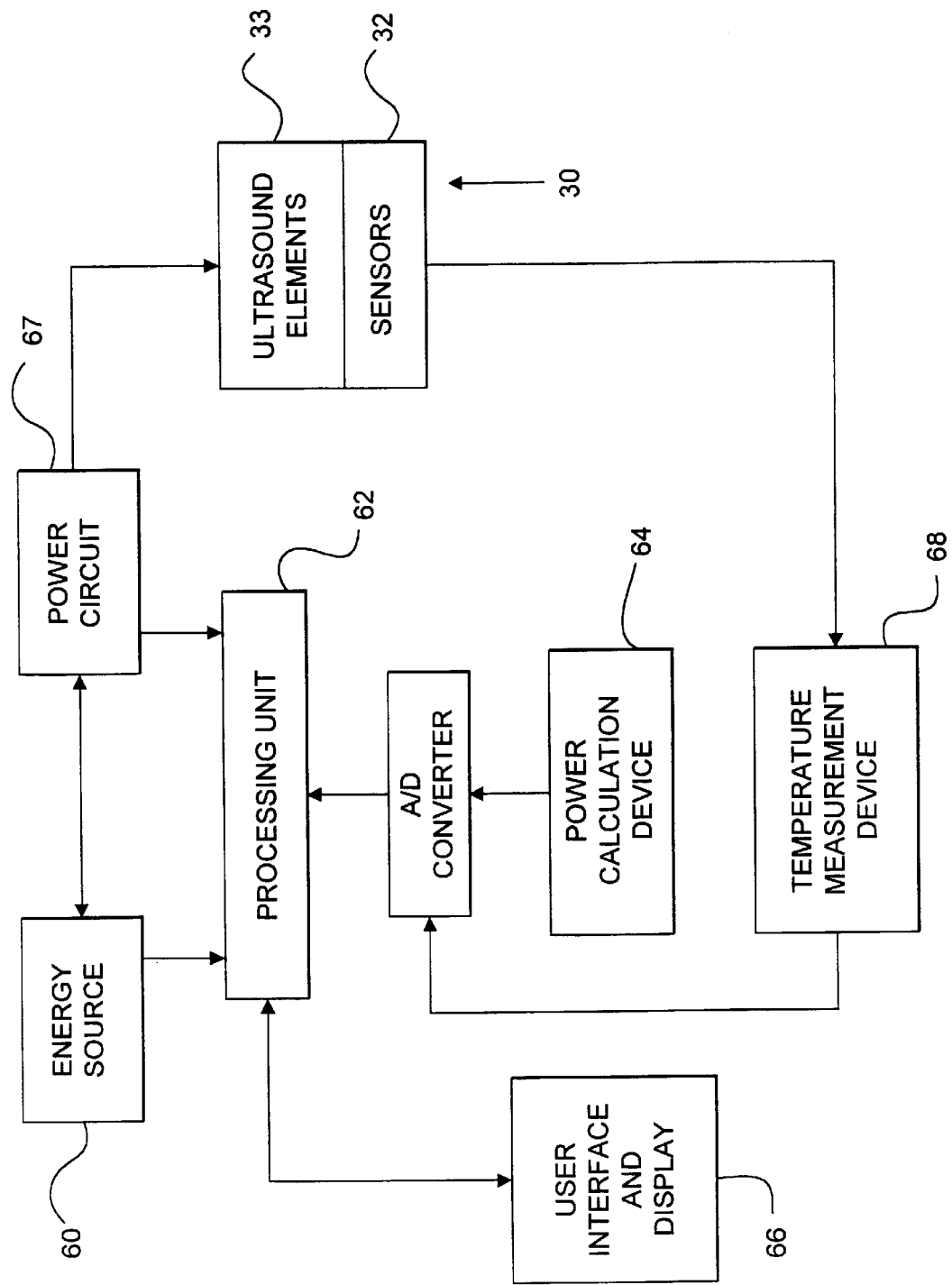
FIG. 6 is a schematic of a feedback control system for a catheter including a plurality of ultrasound elements.

The catheter can be coupled with an open or closed loop feedback system. Referring now to FIG. 6 an open or closed loop feedback system couples temperature sensor 33 to an energy source 60. The temperature of the tissue, or of each ultrasound element 32 is monitored, and the output power of energy source 60 adjusted accordingly. The physician can, if desired, override the closed or open loop system. A processing unit 62 can be included and incorporated in the closed or open loop system to switch power on and off, as well as modulate the power. The processing unit 62 includes logic for monitoring the temperature at each temperature sensor 33, adjusting the power delivered to each ultrasound element 32, re-monitoring the temperature at each temperature sensor 33 and re-adjusting the power delivered to the ultrasound elements 32 in response to the re-monitored temperature.

With the use of the temperature sensors 33 and the feedback control system, the tissue adjacent to the ultrasound elements 32 can be maintained at a desired temperature for a selected period of time. Each ultrasound element 32 is connected to resources which generate an independent output. The output maintains a selected energy at each ultrasound element 32 for a selected length of time.

Power delivered to the ultrasound elements 32 is measured by the power calculation device 64. The power can then be displayed at user interface and display 66. Signals representative of power and impedance values are received by the processing unit 62.

A control signal is generated by the processing unit 62 that is proportional to the difference between an actual measured value, and a desired value. The control signal is used by power circuits 67 to adjust the power output in an appropriate amount in order to maintain the temperature at each ultrasound element 32 within a desired range.

The temperatures detected at the temperature sensors 33 provide feedback for maintaining the desired temperature range. The temperature at each temperature sensor 32 can be used as safety devices to interrupt the delivery of energy when maximum pre-set temperatures are exceeded. The temperature at each ultrasound sensor 32 is measured at temperature measurement device 68, and can be displayed at user interface and display 66. A temperature control signal is generated by the processing unit 62 that is proportional to the difference between an actual measured temperature and a desired temperature. The temperature control signal is used to determine the desired power. For instance, when the control signal exceeds a pre-determined level, the desired power supplied to a particular ultrasound element can be reduced or turned off. Similarly, when the control signal falls below a pre-determined level, the desired power supplied to a particular ultrasound element 12 can be increased or turned on.

The processing unit 62 can be a digital or analog controller, or a computer with software. When the processing unit 62 is a computer it can include a CPU coupled through a system bus. On this system can be a keyboard, a disk drive, or other non-volatile memory systems, a display, and other peripherals, as are known in the art. Also coupled to the bus is a program memory and a data memory.

User interface and display 66 includes operator controls and a display.

The output of the temperature sensors 33 is used by the processing unit 62 to maintain a selected temperature range at each temperature sensor 33. A profile of the power delivered to each ultrasound element 32 can be incorporated in the processing unit 62 and a preset amount of energy to be delivered may also be profiled.

Circuitry, software and feedback to the processing unit 62 result in process control, and the maintenance of the selected power setting that is independent of changes in voltage or current, and used to change, (i) the selected power setting, (ii) the duty cycle (on-off time), (iii) bipolar or monopolar energy delivery and (iv) fluid delivery, including flow rate and pressure. These process variables are controlled and varied, while maintaining the desired delivery of power independent of changes in voltage or current, based on temperatures monitored at the temperature sensor 13.

While the present invention is disclosed by reference to the preferred embodiments and examples detailed above, it is to be understood that these examples are intended in an illustrative rather than limiting sense, as it is contemplated that modifications will readily occur to those skilled in the art, which modifications will be within the scope of the invention.

What is claimed is:

1. A method for performing gene therapy on a selected section of a body lumen comprising:

placing within a selected section of the body lumen a catheter including one or more expandable members for occluding sections of the body lumen proximal and/or distal to the selected section;

occluding sections of the body lumen proximal and/or distal to the selected section of the body lumen;

delivering a gene therapy composition into the selected section of the body lumen; and delivering ultrasound to the selected section of the body lumen for a period of time in the presence of the gene therapy composition under conditions where the ultrasound causes cavitation of cells in the selected section.

2. The method according to claim 1 wherein the catheter includes an expandable member for occluding a section of the body lumen proximal to the selected section of the body lumen, the method including occluding a section of the body lumen proximal to the selected section of the body lumen.

3. The catheter according to claim 1 wherein the catheter includes an expandable member for occluding a section of the body lumen distal to the selected section of the body lumen, the method including occluding a section of the body lumen distal to the selected section of the body lumen.

4. The method according to claim 1 wherein the catheter includes an expandable member for occluding a section of the body lumen proximal to the selected section of the body lumen and an expandable member for occluding a section of the body lumen distal to the selected section of the body lumen, the method including occluding sections of the body lumen proximal and distal to the selected section of the body lumen.

5. The method according to claim 1 wherein the method further includes the step of washing the selected section of the body lumen before delivering the gene therapy composition into the selected section of the body lumen.

6. The method according to claim 5 wherein the method further includes the step of delivering ultrasound during the washing step.

7. The method according to claim 1 wherein the method further includes the step of washing the selected section of the body lumen after delivering the gene therapy composition into the selected section of the body lumen in order to remove the gene therapy composition from the body lumen.

8. The method according to claim 7 wherein the method further includes the step of delivering ultrasound during the washing step.

9. The method according to claim 1 wherein the gene therapy agent is selected from the group consisting of DNA and RNA viral vectors and plasmids.

10. The method according to claim 1 wherein the gene therapy composition further includes a microbubble booster.

11. The method according to claim 1 wherein the gene therapy composition further includes a gene therapy carrier.

12. The method according to claim 1 wherein the step of delivering ultrasound is performed intermittantly with the step of delivering the gene therapy composition.

13. The method according to claim 12 wherein the step of delivering ultrasound intermittantly includes ceasing delivery of ultrasound for periods of time at least 0.1 second in duration.

14. The method according to claim 12 wherein the step of delivering ultrasound intermittantly includes ceasing delivery of ultrasound for periods of time sufficient for a bolus of the gene therapy composition to be delivered from a location in the catheter where the composition is not affected by the prior delivery of ultrasound to the selected section.

* * * * *

UNITED STATES PATENT AND TRADEMARK OFFICE
CERTIFICATE OF CORRECTION

PATENT NO.: 6,135,976

DATED: October 24, 2000

INVENTOR: Tachibana et al.

It is certified that error appears in the above-identified patent and that said Letters Patent is hereby corrected as shown below:

ON THE TITLE PAGE

Item [75] Inventors: delete "Cozier Tachibana" and insert:

--Katsuro Tachibana--.

Signed and Sealed this

Eighth Day of May, 2001

*Attest:*

NICHOLAS P. GODICI

*Attesting Officer*  *Acting Director of the United States Patent and Trademark Office*